US012048765B2

(12) United States Patent
Maspoch Comamala et al.

(10) Patent No.: US 12,048,765 B2
(45) Date of Patent: Jul. 30, 2024

(54) LIPOSOME-BASED IMMUNOTHERAPY

(71) Applicants: FUNDACIÓ INSTITUT D'INVESTIGACIÓ EN CIENCIES DE LA SALUT GERMANS TRIAS I PUJOL, Badalona (ES); FUNDACIÓ INSTITUT CATALÀ DE NANOCIÈNCIA I NANOTECNOLOGIA, Bellaterra (ES); INSTITUCIÓ CATALANA DE RECERCA I ESTUDIS AVANATS, Barcelona (ES)

(72) Inventors: Daniel Maspoch Comamala, Sant Cugat del Vallès (ES); Antonia Maria Cano Sarabia, Alguazas (ES); Marta Vives Pi, Barcelona (ES); Irma Pujol Autonell, Sant Vicenç de Torelló (ES); Juan Verdaguer Autonell, Barcelona (ES)

(73) Assignees: FUNDACIO INSTITUT D'INVESTIGACIÓ EN CIÈNCIES DE LA SLUT GERMANS TRIAST PUJOL, Badalona (ES); FUNDACIÓ INSTITUT CATALÀ DE NANOCIÈNCIA I NANOTECNOLOGIA, Bellaterra (ES); INSTITUCIÒ CATALANA DE RECERCA I ESTUDIS AVANCATS, Barcelona (ES)

( * ) Notice: Subject to any disclaimer, the term of this patent is extended or adjusted under 35 U.S.C. 154(b) by 0 days.

(21) Appl. No.: 15/111,466

(22) PCT Filed: Jan. 16, 2015

(86) PCT No.: PCT/EP2015/050747
§ 371 (c)(1),
(2) Date: Jul. 13, 2016

(87) PCT Pub. No.: WO2015/107140
PCT Pub. Date: Jul. 23, 2015

(65) Prior Publication Data
US 2016/0338953 A1    Nov. 24, 2016

(30) Foreign Application Priority Data
Jan. 17, 2014 (EP) .................... 14151629

(51) Int. Cl.
*A61K 39/00* (2006.01)
*A61K 9/127* (2006.01)

(52) U.S. Cl.
CPC .......... *A61K 9/127* (2013.01); *A61K 39/0008* (2013.01); *A61K 2039/577* (2013.01)

(58) Field of Classification Search
None
See application file for complete search history.

(56) References Cited

U.S. PATENT DOCUMENTS

| 8,920,774 | B2 | 12/2014 | Ishii et al. |
| 9,265,815 | B2 * | 2/2016 | Fraser .................... A61K 39/00 |
| 9,333,244 | B2 * | 5/2016 | Li ........................ A61K 9/0034 |
| 2012/0164189 | A1 | 6/2012 | Balu-Iyer et al. |
| 2013/0251786 | A1 | 9/2013 | Li et al. |

FOREIGN PATENT DOCUMENTS

| EP | 1547581 A1 | 6/2005 |
| WO | WO0224162 A1 | 3/2002 |
| WO | WO2007014754 A1 | 2/2007 |
| WO | 2009/101207 A1 | 8/2009 |

OTHER PUBLICATIONS

Pugliese, A. Immunology 2004;111:138-146.*
Peakman, M. et al. Immunology 2001;104:361-366.*
Smith, E.L. and Peaknan, M. Frontiers Immunol. 2018; 9:1-5.*
Huynh, M.L.N., et al. J. Clin. Invest. 2002;109(1):41-50.*
Marin-Gallen, et al., "Dendritic cells pulsed with antigen-specific apoptotic bodies prevent experimental type 1 diabetes," *Clin Exp Immunol* 2009, vol. 160, pp. 207-214.
Alba, et al., "IFN beta accelerates autoimmune type 1 diabetes in nonobese diabetic mice and breaks the tolerance to beta cells in nondiabetes-prone mice," *J Immunol* 2004, vol. 173, pp. 6667-6675.
Pujol-Autonell, et al., "Efferocytosis promotes suppresive effects in dendritic cells through prostaglandin E2 production in the context of autoimmunity," *Plos One* 2013, vol. 8, Issue 5, pp. 1-10.
Ulrich, Anne S., "Biophysical aspects of using liposomes as delivery vehicles," *Bioscience Reports* 2002, vol. 22, No. 2, pp. 129-150.
Maurer, et al., "Developments in liposomal drug delivery systems," *Expert Opin Biol Ther* 2001, vol. 1:6, pp. 923-947.

(Continued)

*Primary Examiner* — G. R. Ewoldt
(74) *Attorney, Agent, or Firm* — SQUIRE PATTON BOGGS (US) LLP

(57) ABSTRACT

The present invention provides a liposome encapsulating an autoantigen, wherein the liposome has a size comprised from 500 to 15000 nm and the liposome membrane comprises phosphatydilserine (PS) in an amount comprised from 10 to 40% by weight with respect to the total membrane liposomal composition. Pharmaceutical or veterinary compositions comprising a therapeutically effective amount of said liposome are also provided. Further, the invention provides liposomes and pharmaceutical or veterinary compositions as defined above for use as a medicament, particularly for the treatment of autoimmune diseases. Finally the present invention provides liposomes and pharmaceutical or veterinary compositions as defined above for use in the restoration of tolerance to self in a patient suffering from an autoimmune disease.

14 Claims, 9 Drawing Sheets

Specification includes a Sequence Listing.

(56) References Cited

OTHER PUBLICATIONS

Waterhouse, et al., "Preparation, characterization, and biological analysis of liposomal formulations of vincristine," *Methods Enzymol.* 2005, vol. 391, pp. 40-57.
Urban, et al., "Study of the efficacy of antimalarial drugs delivered inside targeted immunoliposomal nanovectors," *Nanoscale Research Letters* 2011, vol. 6, p. 620 (9 pages).
Roep, Bart O., and Mark Peakman, "Antigen Targets of Type 1 Diabetes Autoimmunity," *Cold Spring Harb Perspect Med* 2012, vol. 2:a007781 (14 pages).
Lernmark, Åke, "Autoimmune diseases: are markers ready for prediction?," *J. Clin Invest* 2001, vol. 108, pp. 1091-1096.
Espejo, et al., "Treatment with anti-interferon-gamma monoclonal antibodies modifies experimental autoimmune encephalomyelitis in interferon-gamma receptor knockout mice," *Exp Neurol* 2001, vol. 172, pp. 460-468.
Strejan, et al., "Suppression of Experimental Allergic Encephalomyelitis in Lewis Rats Treated with Myelin Basic Protein-Liposome Complexes: Clinical, Histopathological, and Cell.Mediated Immunity Correlates," *Cellular Immunology* 1984, vol. 84, pp. 171-184.
Wu, Zhou and Iiroshi Nakanishi, "Phosphatidylserine-containing liposomes: Potential pharmacological interventions against inflammatory and immune diseases through the production of prostaglandin E2 after uptake by myeloid derived phagocytes," *Arch. Immunol. Ther. Exp.* 2011, vol. 59, pp. 195-201.
Harel-Adar, Tamar, et al., "Modulation of cardiac macrophages by phosphatidylserine-presenting liposomes improves infarct repair," *PNAS*, Feb. 1, 2011, vol. 8, No. 5, pp. 1827-1832.
Pujol-Autonell, Irma, et al., "Use of Autoantigen-Loaded Phophatidylserine-Liposomes to Arrest Autoimmunity in Type 1 Diabetes," *PLOS One*, Jun. 3, 2015, vol. 10, No. 6, 19 pages.
Rodriguez-Fernandez, Silvia, et al., "Phosphatidylserine-Liposomes Promote Tolerogenic Features on Dendritic Cells in Human Type 1 Diabetes by Apoptotic Mimicry," *Frontiers in Immunology*, Feb. 14, 2018, vol. 9, Art. 253, 17 pages.
Pugliese, "Insulin: a critical autoantigen and potential therapeutic agent in Type 1 diabetes", Expert Rev. Clin. Immunol. 2006, vol. 2, No. 3, pp. 419-431.
McFarland, et al., "Multiple sclerosis: a complicated picture of autoimmunity", Nature Immunology Sep. 2007, vol. 8, No. 9, pp. 913-919.
Pujol-Autonell, et al., "Liposome-based immunotherapy against auoimmune diseases: therapeutic effect on multiple sclerosis", Nanomedicine (Lond.), May 18, 2017, vol. 12, No. 11, pp. 1231-1242.
Babaya, et al: "Murine High Specificity/Sensitivity Competitive Europium Insulin Autoantibody Assay", Diabetes Technology & Therapeutics 2009, vol. 11, No. 4, pp. 227-233.
Dhuria, et al: "Current status and patent prospective of animal models in diabetic research", Review Article, Advanced Biomedical Research 2015, vol. 4, No. 117, pp. 1-14.
Dumont, et al: "MINIREVIEW Mechanism of action of the immunosuppressant Rapamycin", Life Sciences 1996, vol. 58 No. 5, pp. 373-395.
Eizirik, et al: "The role of inflammation in insulitis and B-cell loss in type 1 diabetes", Nature Reviews, Endocrinology, Apr. 2009, vol. 5, pp. 219-226.
Fadok, et al: "Macrophages that have ingested apoptotic cells in vitro inhibit inflammatory cytokine production through autocrine/paracrine mechanisms involving TGF-beta, PGE2, and PAF", The Journal of Clinical Investigation 1998, vol. 101, No. 4, pp. 890-898.
Giannoukakis, et al: "Phase I (Safety) Study of Autologous Tolerogenic Dendritic Cells in Type 1 diabetes patients", Diabetes Care Sep. 2011, vol. 34, pp. 2026-2032.
Hancock, et al: "Short Communication Suppression of insulitis in non-obese diabetic (NOD) mice by oral insulin administration is associated with selective expression of Interleukin-4 and -10, transforming Growth Factor-B, and Prostaglandin-E", American Journal of Pathology Nov. 1995, vol. 147, No. 5, pp. 1193-1199.
Machen, et al: "Antisense Oligonucleotides down-regulating costimulation confer diabetes-preventive properties to nonobese diabetic mouse dendritic cells", The Journal of Immunology 2004, vol. 173, pp. 4331-4341.
Marin-Gallen, et al: "Dendritic cells pulsed with antigen-specific apoptotic bodies prevent experimental type 1 diabetes", British Society for Immunology 2009, Original Article, Clinical and Experimental Immunology, vol. 160 pp. 207-214.
O'Brien, et al: "A deficiency in the vivo of a apoptotic cells is a feature of the NOD mouse", Journal of Autoimmunity 2006, vol. 26, pp. 104-115.
Pujol-Autonell, et al: "Use of autoantigen-loaded phosphatidylserine-liposomes to arrest autoimmunity in Type 1 diabetes", Research Article, PLOS One, Jun. 3, 2015, pp. 1-19.
Shoda, et al: "A Comprehensive Review of interventions in the NOD mouse and implications for translation", Immunity Aug. 2005, vol. 23, pp. 115-126.
Turnquist, et al: LEGENDplex Multi-Analyte Flow Assay Kits "Rapamycin-conditioned dendritic cells are poor stimulators of allogeneic CD4+T Cells, but enrich for antigen-specific Foxp3+T egulatory cells and promote organ transplant tolerance", The Journal of Immunology 2014, pp. 7018-7031.

\* cited by examiner

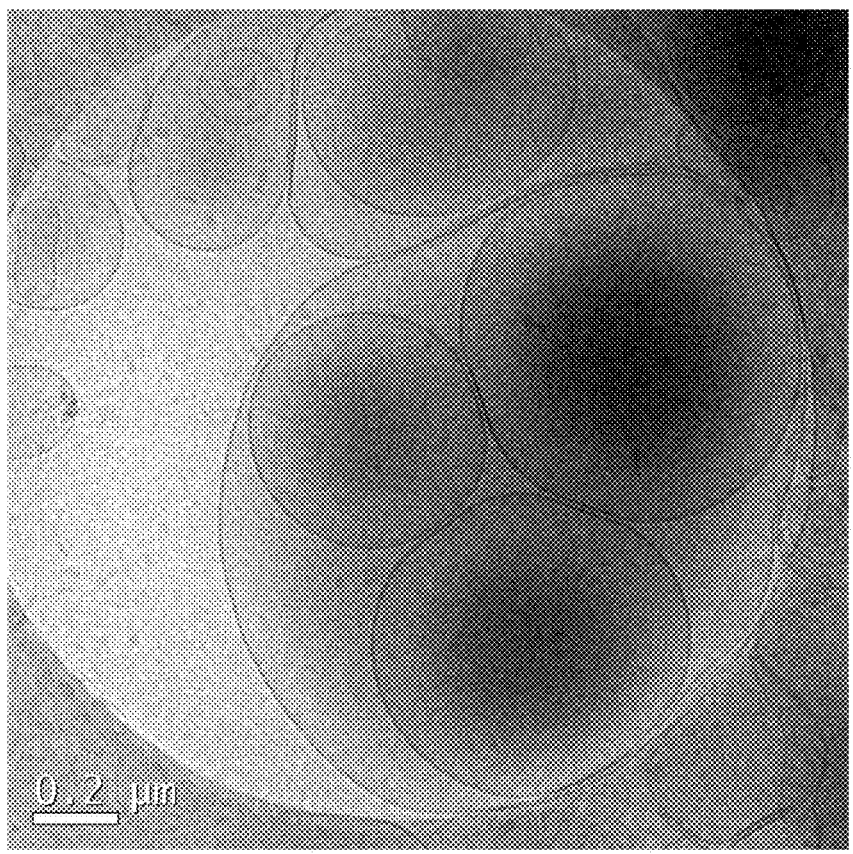
FIG.1: Cryogenic transmission electron microscopy (cryo-TEM, JEOL-JEM 1400 microscope) images of PS-liposome loaded with insulin-derived autoantigen.

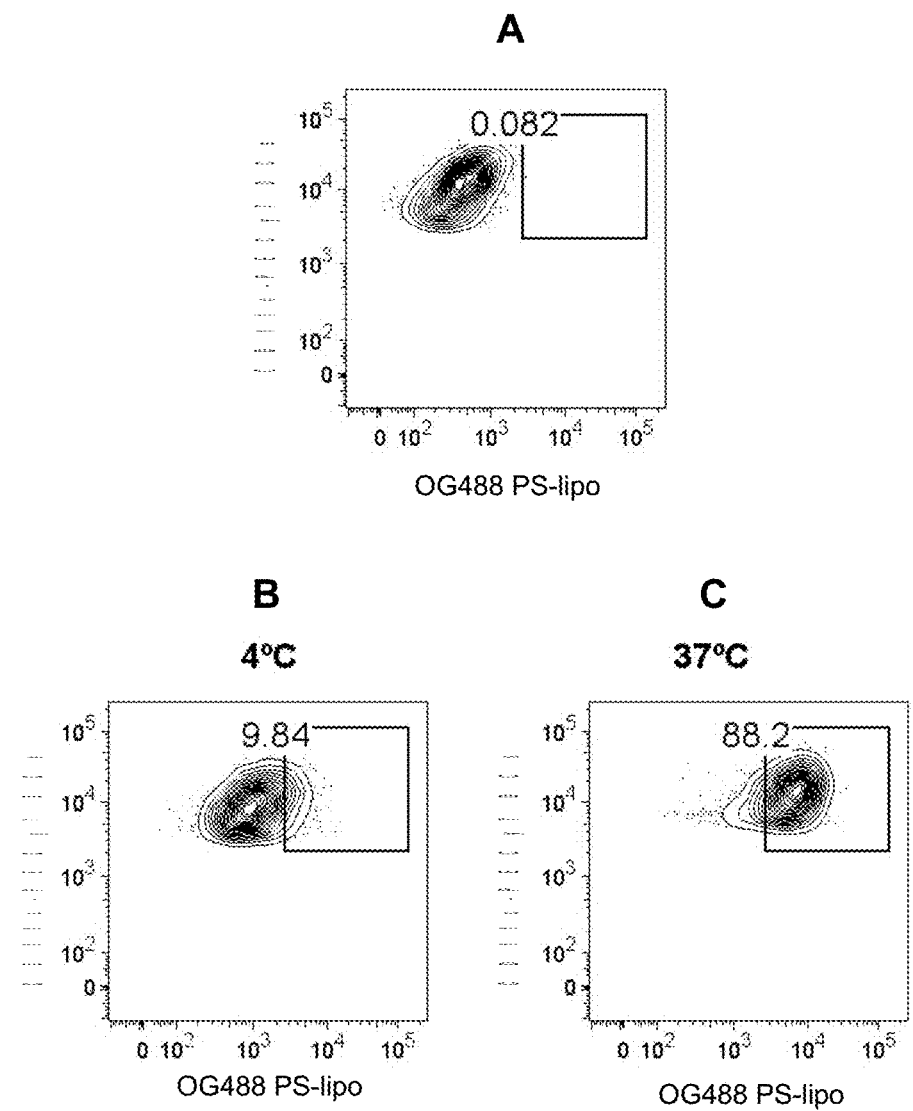
FIG. 2: Flow cytometry (FACS) analysis of control dendritic cells (DCs) (A), DCs co-cultured during 30 minutes with Oregon green 488 DHPE labelled PS-liposomes (OG488 PS-lipo) at 4°C (B) and at 37°C (C).

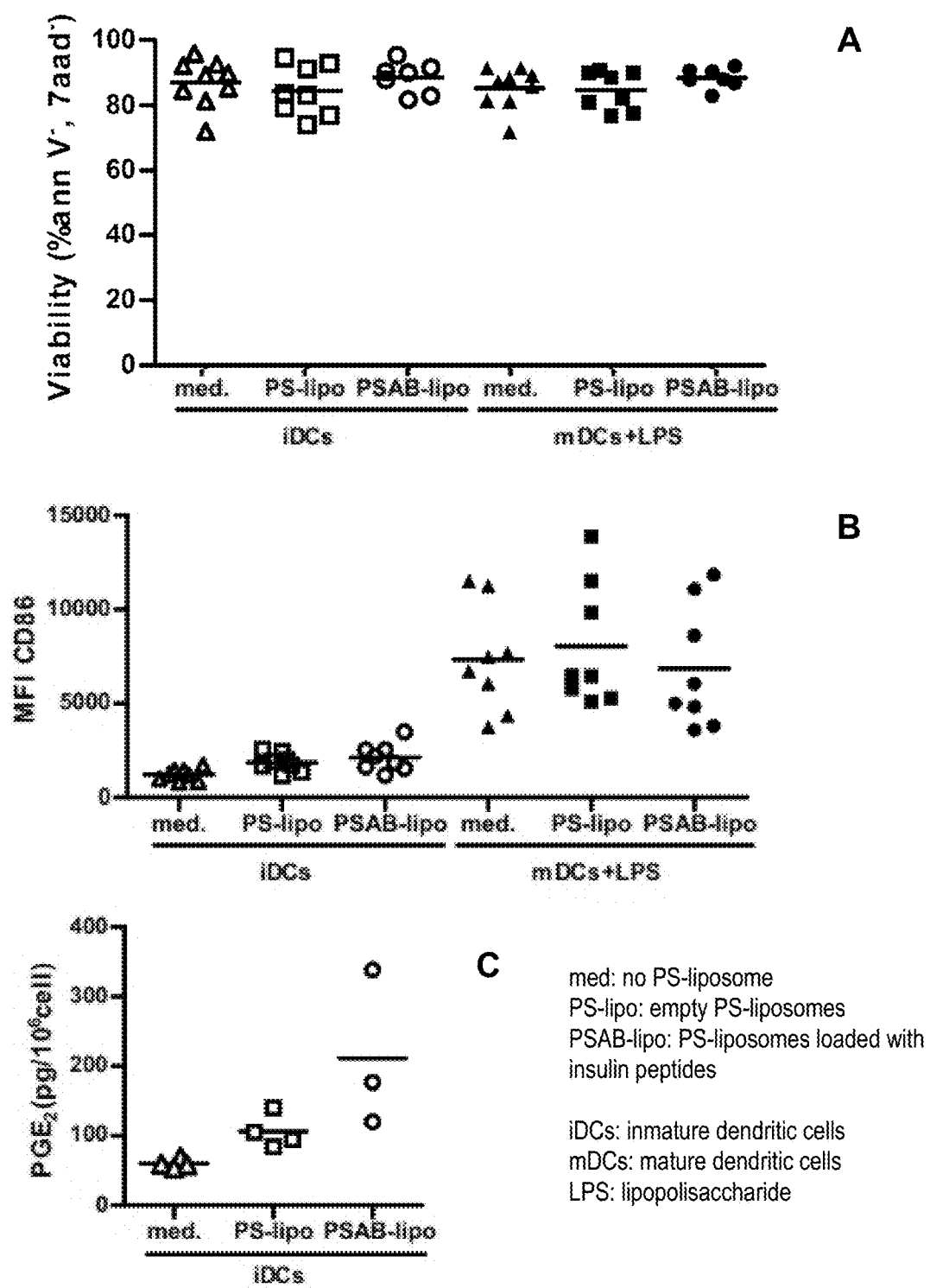
FIG. 3. Effects of the capture of PS-liposomes in dendritic cells (DCs). (A) DCs viability (%), (B) median of fluorescence intensity for CD40 and CD86 membrane expression and (C) quantification of the production of Prostaglandin E2 (PGE2)

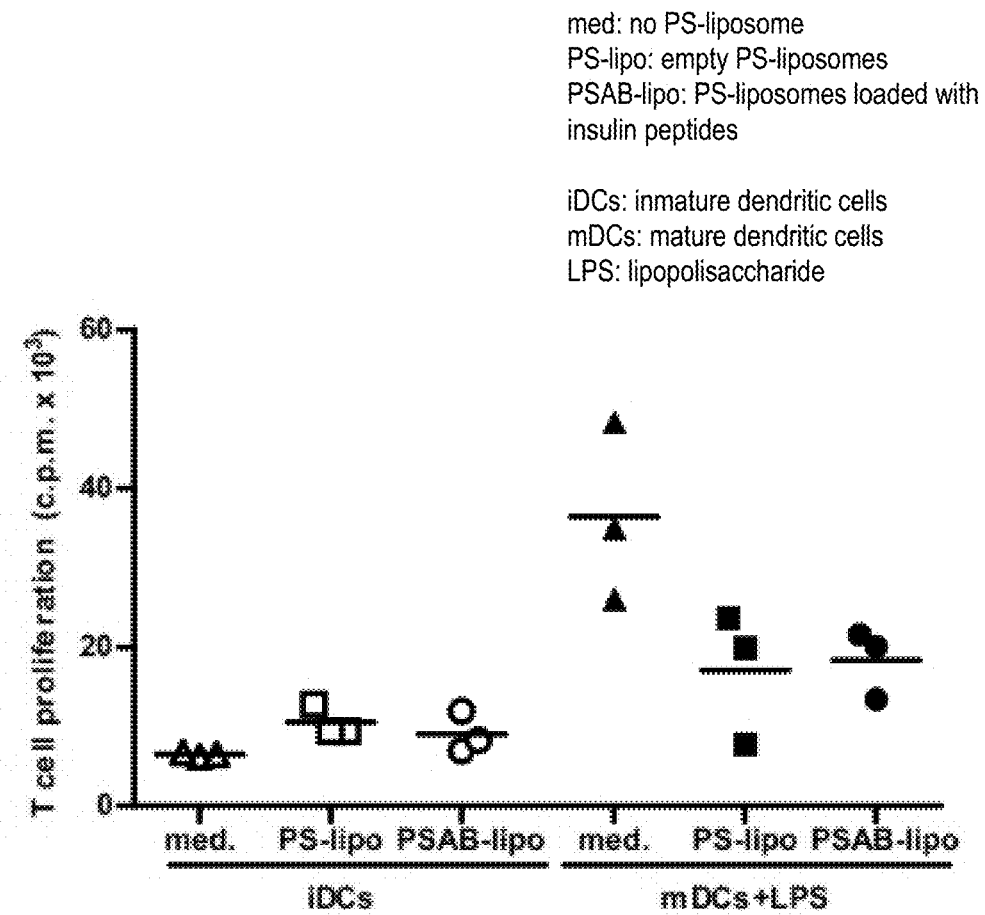
FIG. 4: Impaired ability of DCs to stimulate autologous T cell proliferation after the capture of PS-liposomes, even after proinflammatory stimuli.

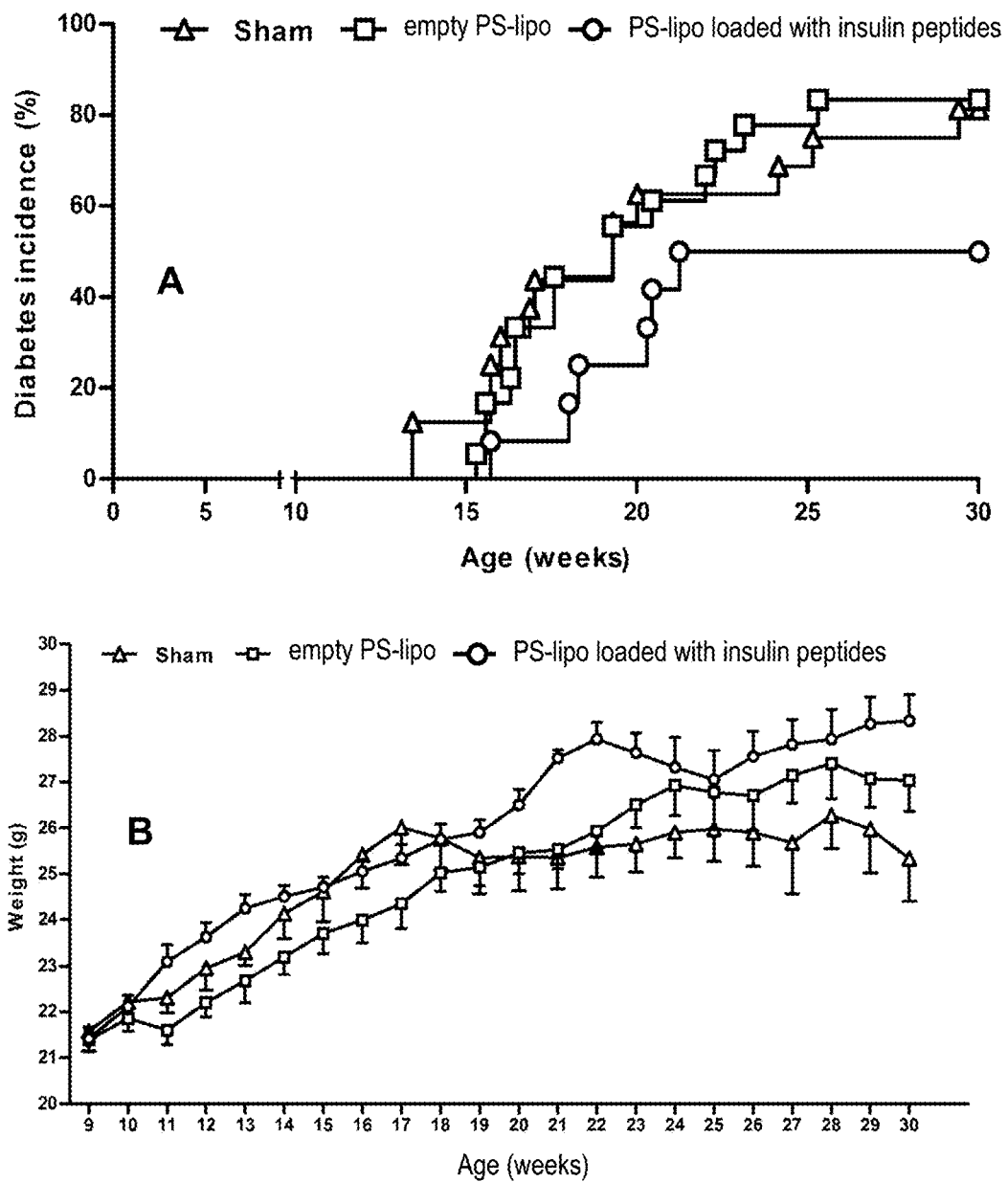
FIG. 5: Immunotherapy using PS-liposome encapsulated insulin peptides decreases T1D incidence in NDO mice. (A) cumulative incidence (percentage) of diabetes. (B) follow up of body weight.

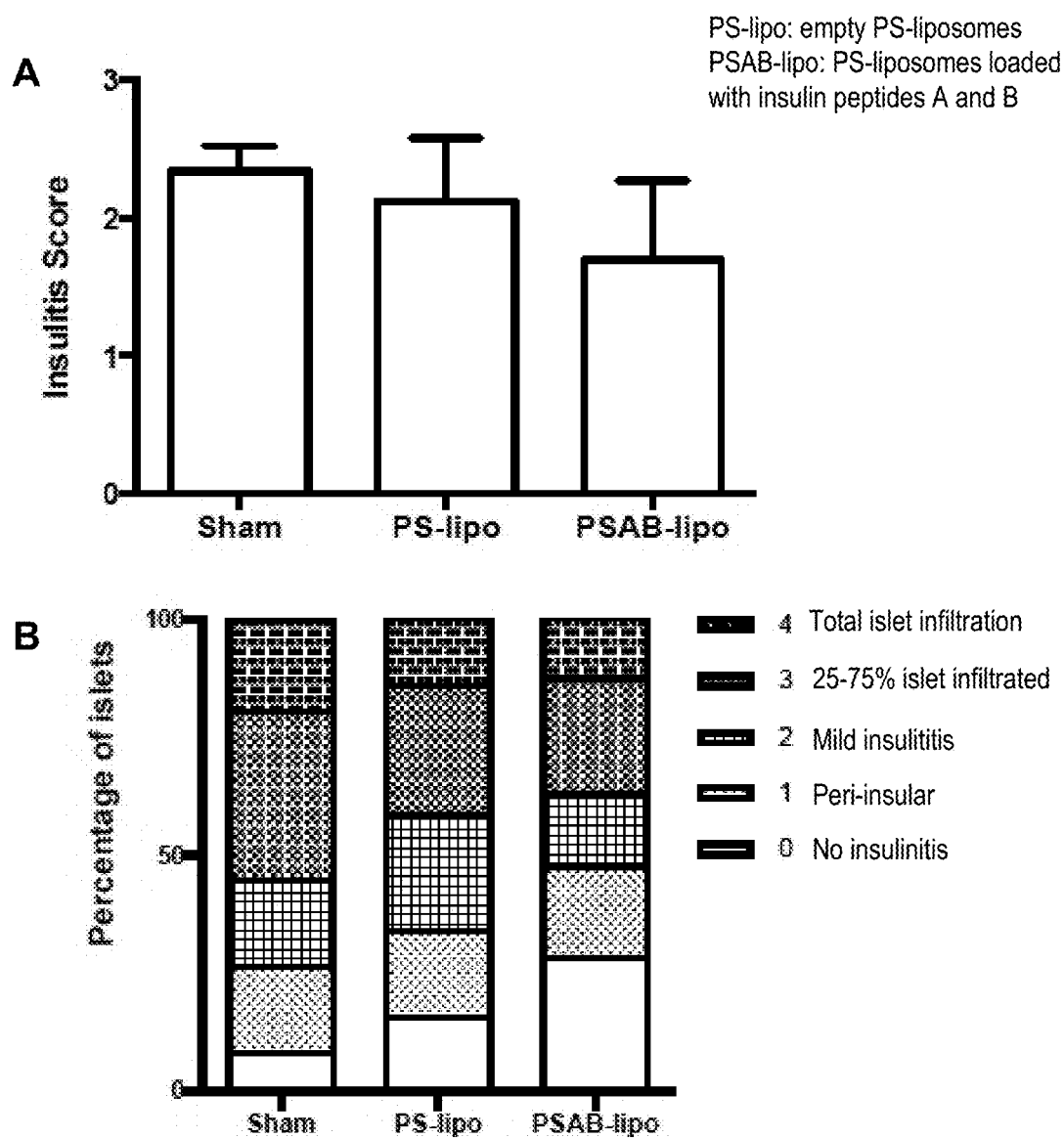
FIG. 6: Effect of PS-liposomes on insulitis in NOD mice. (A) insulitis score for different groups of NOD mice and (B) percentage of islets classified in each of the five infiltration categories in different NOD mice groups.

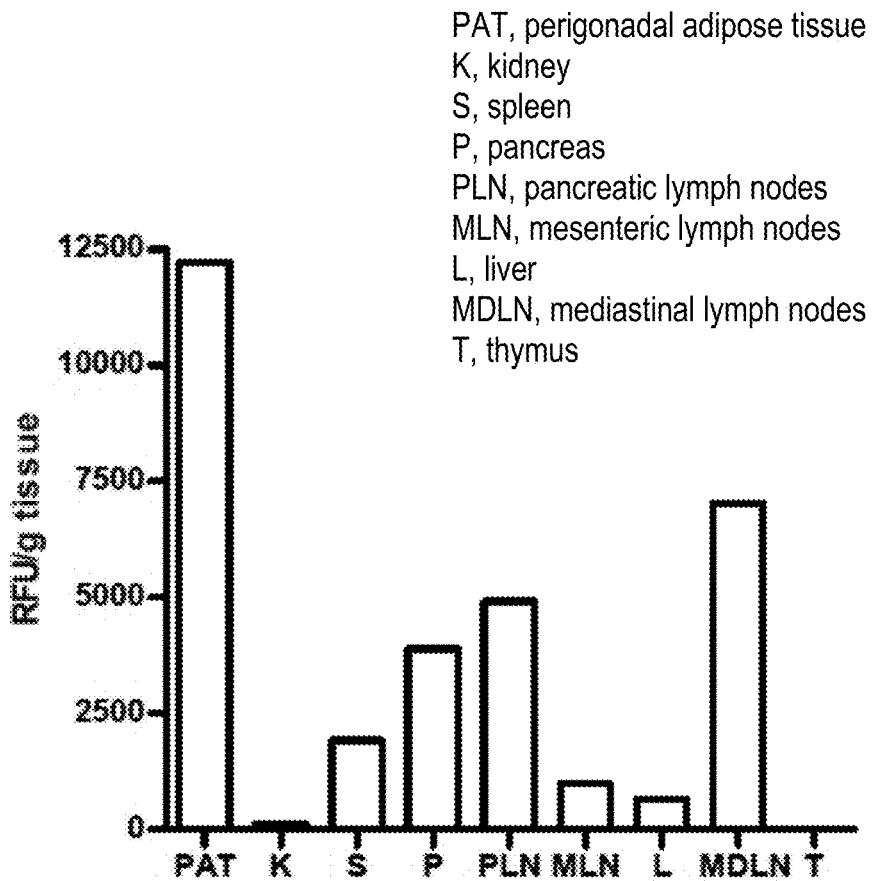
FIG. 7: Tracking of PS-liposomes. Histogram of fluorescent signal (RFU, Relative Flourescence Units / g of tissue) in several organs from NOD mice intraperitoneal (i.p.) injected with fluorescence labeled PS-liposomes.

A
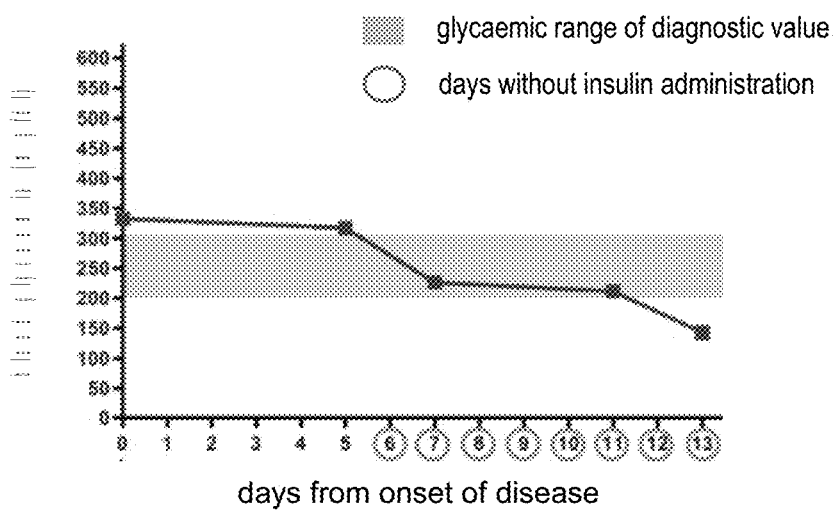
B
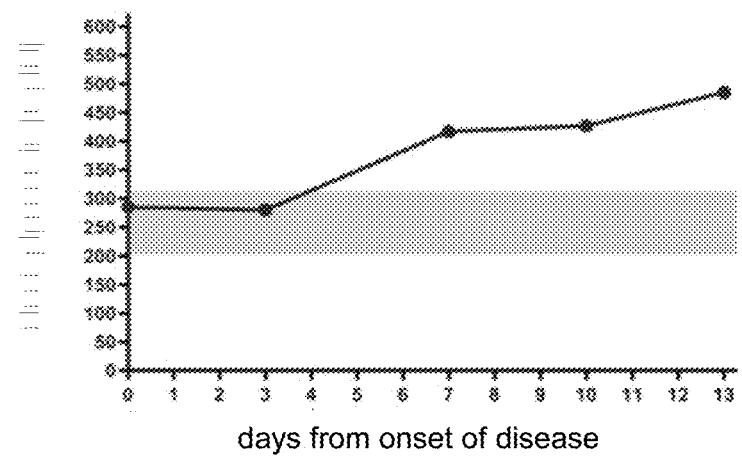
FIG. 8: Levels of glycaemia in diabetic mice treated with PS-liposomes loaded with insulin peptides (A) or empty liposomes (B)

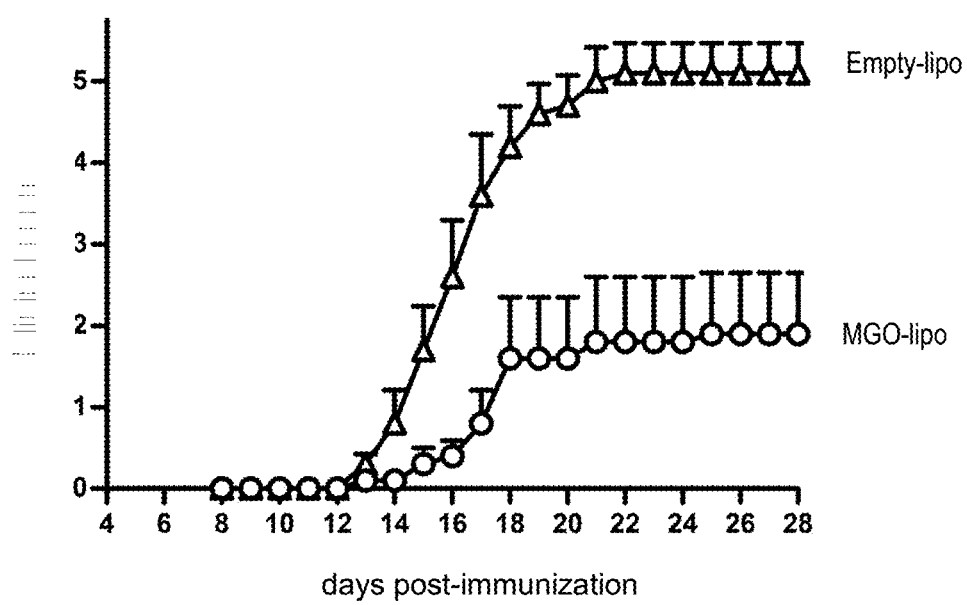
FIG. 9: Clinical score of EAE performed daily for C57BL/6 immunized mice treated with liposomes containing MOG peptide or empty liposomes.

LIPOSOME-BASED IMMUNOTHERAPY

CROSS-REFERENCE TO RELATED APPLICATION

This application is a U.S. national phase entry of International Patent Application No. PCT/EP2015/050747, filed Jan. 16, 2015, which in turn claims priority to European Patent Application No. 14151629.4, filed Jan. 17, 2014. Each of the foregoing applications is incorporated herein by reference in its entirety.

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "P2898US00_seq_list_ST25.txt." created Jul. 11, 2016, and is 1384 bytes in size. The sequence listing contained in this .txt file is part of the specification and is incorporated herein by reference in its entirety.

The present invention relates to the field of medicine. In particular, the present invention provides autoantigen-encapsulating liposomes for the prevention or treatment of autoimmune disorders.

BACKGROUND ART

Autoimmunity is the failure of an organism in recognizing its own constituent parts as self, thus leading to an immune response against its own cells and tissues. Any disease that results from an aberrant immune response is termed an autoimmune disease. Prominent examples include type 1 diabetes (T1D), lupus erythematosus, rheumatoid arthritis, multiple sclerosis (MS), Addison's disease, celiac disease, dermatomyositis, Hashimoto's thyroiditis, myasthenia gravis, pernicious anemia, reactive arthritis, Sjogren syndrome.

It is calculated that 7 to 10% of the population in developed countries of the population suffers from these diseases, which are often chronic, debilitating, and life-threatening. Autoimmune-associated medical care costs continue to scale up as autoimmune disorders increase world-wide and no effective treatments are made available.

Treatments for autoimmune disease have traditionally been immunosuppressive, anti-inflammatory (steroids), or palliative. Non-immunological therapies, such as hormone replacement in Hashimoto's thyroiditis or Type 1 diabetes mellitus, treat outcomes of the autoaggressive response, thus these are palliative treatments. Dietary manipulation limits the severity of celiac disease. Steroidal or NSAID treatment limits inflammatory symptoms of many diseases.

Extensive research has been invested in the development of immunomodulating therapies that reduce or avoid the undesired immune response. However, the limited understanding of the intricate details of the different autoimmune diseases substantially slows down progress in this field. Current strategies are generally based on broad-acting immunosuppressive drugs which, in order to maintain immunosuppression, are generally life-long treatments. Additionally, the use of broad-acting immunosuppressants is associated with a risk of severe side effects, such as tumors, infections, nephrotoxicity and metabolic disorders.

In spite of the efforts made until now, there is still the need of further therapeutical approaches to treat autoimmune disorders which are effective and devoid of undesired side effects.

SUMMARY OF THE INVENTION

The inventors have developed a new autoantigen-specific therapy which is highly effective in the treatment of autoimmune diseases. In particular, the inventors have found that an autoimmune disease may be effectively treated by encapsulating the autoantigen(s) associated with the autoimmune disease intended to be treated in a liposome with specific size and comprising the lipid phosphatidylserine.

In a first aspect the present invention thus relates to a liposome encapsulating an autoantigen, wherein (i) the liposome has a size comprised from 500 to 15000 nm; and (ii) the liposome membrane comprises phosphatydilserine (PS) in an amount comprised from 10 to 40% by weight with respect to the total membrane liposomal composition.

The present inventors have found that the particular features of the liposome of the invention, i.e. a size comprised from 500 to 15,000 nm and the presence of 10 to 40% PS, enable the tolerogenic presentation of the encapsulated autoantigen by antigen presenting cells, thereby restoring tolerance to the autoantigen.

Without wishing to be bound by theory, the inventors hypothesize that the specific features of the present liposomes ensure that they are effectively engulfed by dendritic cells and the encapsulated autoantigen is processed and presented to CD4+T lymphocytes through MHC class II molecules (exogenous presentation) and to CD8+T lymphocytes (crosspresentation) in tolerogenic forms, thus inducing tolerance to the antigen and arresting the autoimmune cascade. Otherwise stated, the autoantigen-encapsulating liposome of the present invention induces tolerance to the autoantigen rather than autoimmunity, which results in the effective treatment of the autoimmune disorder.

The tolerogenic effect of the autoantigen-encapsulating liposome of the invention and its surprising effect in the treatment of the autoimmune disorder, particularly, in the treatment of T1D and MS, are demonstrated in the examples below.

As shown in FIGS. 2, 3 and 4, PS-liposomes encapsulating insulin peptides are captured by dendritic cells, whereby these dendritic cells acquire tolerogenic features: decreased expression of co-stimulatory molecules, induced PGE2 production and decreased T cell proliferation in the context of diabetes. The results indicate that the liposomes, to some extent, promote tolerogenicity of dendritic cells (DCs) similar to apoptotic bodies. In addition, the effect was not diminished after a proinflammatory stimulus, an important feature to take into account because it demonstrates that the therapy is effective once the autoimmune cascade is on-going and pro-stimulatory stimuli are present.

All the above results in efficient treatment of autoimmune disease, as shown in the examples below. FIGS. 5 and 6 demonstrate that treatment of NOD pre-diabetic mice is achieved within a single administration of the liposomes of the invention, while FIG. 8, A, shows that PS-liposomes loaded with insulin peptides may revert diabetes in NOD mice when administered after the onset of the disease. Further, FIG. 9 shows that PS-liposomes containing myelin oligodendrocyte glycoprotein (MOG) peptide may prevent the development of experimental autoimmune encephalomyelitis (EAE) disease in C57BL/6 immunized mice. Thus, in contrast to known immunomodulatory or anti-inflammatory treatments for autoimmune disorders, the liposome-based therapy developed by the inventors is not required permanently. Instead, long-lasting restoration of tolerance is achieved, which results in the effective prevention or treatment of the autoimmune disease. This effect can be achieved after a single administration, or alternatively within 2-4 administrations, of a pharmaceutical composition comprising an effective amount of autoantigen-encapsulating liposomes.

It can be also observed in FIGS. 5, 6 and 8, B, that no effect was obtained in T1D incidence when mice received empty liposomes. Thus, the treatment is only effective when the liposomes encapsulate an appropriate autoantigen, which demonstrates the antigen specificity of the nanotherapy.

While being an antigen-specific based therapy, the autoantigen-encapsulating liposome of the invention has the advantage of presenting no undesired side effects. As mentioned above, other immunomodulatory approaches for the treatment of autoimmune diseases involve immunosuppressants, which often lead to high susceptibility to infections and sometimes also promote the development of tumors, nefrotoxicity or metabolic disorders.

On top of affording a tolerogenic presentation, encapsulating the autoantigens in the specifically designed liposomes of the invention is a highly desirable goal because of protection of the cargo from degradation and the decrease/absence of toxicity. This is due to the fact that the autoantigen is confined in the liposome until uptake by antigen presenting cells and, consequently, it may not induce an adverse immune response.

A second aspect of the invention provides a pharmaceutical or veterinary composition comprising a therapeutically effective amount of the autoantigen-encapsulating liposome as defined above together with other appropriate pharmaceutically or veterinary acceptable excipients or carriers.

The liposome-based pharmaceutical composition of the invention has several advantages in terms of stability, uniformity, and ease of large-scale production.

First of all, the production of the present autoantigen-encapsulating liposomes may be achieved using common reagents and equipment in the pharmaceutical industry at a low cost.

The liposomes of the invention, due to their size, are highly stable in solution and easy to obtain, in contrast to smaller liposomes, which tend to aggregate and their production requires repeated extrusion processes through expensive membranes with small pore sizes.

Further, uniformity of the product can be guaranteed, at the same time that scaling-up for large industrial production is affordable.

Another great advantage lies in the fact that the present liposome-based pharmaceutical composition is a defined composition, which is devoid of undesired contaminants or by-products. The autoantigen-encapsulating liposomes do not degenerate into toxic side products, such as necrotic bodies, and do not cause rejections as in the case of autologous or heretologous cell-based therapies.

Thanks to its tolerogenic effect, the autoantigen-encapsulating liposome of the invention affords effective prevention of autoimmune disorders (i.e. avoiding that autoimmunity is triggered), as well as effective treatment of the autoimmune disease both in a pre-clinical stage (i.e. a stage where autoimmunity is already triggered but tissue damage and clinical symptoms are low) and clinical stage (i.e. a stage where tissue damage is higher and clinical symptoms are evident).

Thus, in a third aspect the present invention provides an autoantigen-encapsulating liposome according to the first aspect of the invention for use as a medicament. This aspect can also be formulated as a method for the prevention or treatment of a disease which comprises administering to a mammal in need of such treatment, including a human, a therapeutically effective amount of the autoantigen-encapsulating liposome of the present invention, together with one or more appropriate pharmaceutically acceptable excipients or carriers.

In a fourth aspect, the present invention provides an autoantigen-encapsulating liposome as defined above for use in the prevention or treatment of an autoimmune disease. This aspect can be formulated as the use of an autoantigen-encapsulating liposome as defined above for the manufacture of a medicament for the prevention or treatment of an autoimmune disease. This aspect can also be formulated as a method for the prevention or treatment of an autoimmune disease comprising administering a therapeutically effective amount of an autoantigen-encapsulating liposome as defined above, together with pharmaceutically acceptable excipients or carriers, in a subject in need thereof, including a human.

In a fifth aspect, the present invention provides an autoantigen-encapsulating liposome as defined above for use in the restoration of tolerance to self in a patient suffering from an autoimmune disease. This aspect can be formulated as the use of an autoantigen-encapsulating liposome as defined above for the manufacture of a medicament for the restoration of tolerance to self in a patient suffering from an autoimmune disease. This aspect can also be formulated as a method for the restoration of tolerance to self in a patient suffering from an autoimmune disease comprising administering a therapeutically effective amount of an autoantigen-encapsulating liposome as defined above, together with pharmaceutically acceptable excipients or carriers, in a subject in need thereof, including a human.

Finally, other aspects of the invention provide a liposome or a pharmaceutical or veterinary composition as defined above for suppressing an autoimmune response; and a liposome or pharmaceutical or veterinary composition as defined above for use in the prevention or treatment of an autoimmune disease, wherein said liposome or pharmaceutical or veterinary composition restores tolerance to the encapsulated autoantigen.

BRIEF DESCRIPTION OF THE DRAWINGS

FIG. 1. Cryogenic transmission electron microscopy (cryo-TEM, JEOL-JEM 1400 microscope) images of PS-liposome loaded with insulin-derived autoantigen. Bar=0.2 µm.

FIG. 2. Flow cytometry (FACS) analysis of control DCs (A), DCs co-cultured during 30 minutes with Oregon green 488 DHPE labelled PS-liposomes (OG488 PS-lipo) at 4° C. (B) and at 37° C. (C). x-coordinates represent OG488 PS-lipo; y-coordinates represent CD11c-PECy7 stained DCs.

FIG. 3. Effects of the capture of PS-liposomes in DCs. y-coordinates represent (A) DCs viability (%) assessed by annexin V and 7aad staining, (B) median of fluorescence intensity for CD40 and CD86 membrane expression and (C) quantification of the production of Prostaglandin E2 (PGE2) by ELISA in culture supernatants for immature and mature DCs. White symbols represent immature DCs, before (triangles) and after the capture of PS-liposomes (squares) or PS-liposomes loaded with insulin peptides (circles), 24 hours after culture. Black symbols represent viability of mature DCs before (triangles) and after the capture of PS-liposomes (squares) or PS-liposomes loaded with insulin peptides (circles), 24 hours after proinflammatory stimulus (lipospolysaccharide, LPS). ELISA data are represented as pg/10$^6$ cells.

FIG. 4. Impaired ability of DCs to stimulate autologous T cell proliferation after the capture of PS-liposomes, even after proinflammatory stimuli. y-coordinate represents autologous proliferation of T cells (c.p.m. for 3H thymidine assay) after stimulation induced by immature DCs, before (white triangles) and after the capture of PS-liposomes (white squares) or PS-liposomes loaded with insulin peptides (20 µg/ml) at a ratio of 1:10 (white circles) for 7 days. Black symbols represent proliferation induced by mature DCs before (black triangles) and after the capture of PS-liposomes (black squares) or PS-liposomes loaded with insulin peptides (black circles), previously activated with proinflammatory stimuli LPS (100 ng/ml).

FIG. 5. Immunotherapy using PS-liposome encapsulated insulin peptides decreases T1D incidence. (A) y-coordinate represents cumulative incidence (percentage) of diabetes in NOD mice treated with PS-liposomes loaded with insulin peptides (circles, n=12), empty PS-liposomes (squares, n=18), and in control group that received saline solution (triangles, n=16). (B) y-coordinate represents the follow up of body weight (g) in mice treated with PS-liposomes loaded with insulin peptides (circles, n=12-6), empty PS-liposomes (squares, n=18-3), and control group treated with saline solution (triangles, n=16-3). x-coordinates indicate mice's age in weeks.

FIG. 6. Insulitis score is less severe in immunized mice. Effect of PS-liposomes on insulitis in NOD mice. y-coordinates represent (A) insulitis score for different groups of NOD mice and (B) percentage of islets classified in each of the five infiltration categories in different NOD mice groups. Infiltration categories: 0, no insulitis; 1, peri-insular; 2, mild insulitis (<25% of the infiltrated islet); 3, 25-75% of the islet infiltrated; 4, total islet infiltration. Groups of NOD mice are: control mice treated with saline solution (S), mice treated with empty PS-liposomes (PS) and mice treated with PS-liposomes containing autoantigens (PSAB). Pancreata from 4-6 non diabetic mice/group were analyzed at the end of the study period (30 weeks). Results are means±SEM. *Significant differences (p<0.05) versus control groups (unpaired t-test).

FIG. 7: Tracking of PS-liposomes. Histogram of fluorescent signal (RFU, Relative Flourescence Units/g of tissue) in several organs from NOD mice intraperitoneal (i.p.) injected with fluorescence labeled PS-liposomes (Alexa Fluor 750) at 24 hours. PAT, perigonadal adipose tissue; K, kidney; S, spleen; P, pancreas; PLN, pancreatic lymph nodes; MLN, mesenteric lymph nodes; L, liver; MDLN, mediastinal lymph nodes; T, thymus. Results of one representative experiment of three independent experiments are shown. Y-coordinate indicates RFU/g tissue.

FIG. 8. Levels of glycaemia in diabetic mice treated with PS-liposomes loaded with insulin peptides (A) or empty liposomes (B) at days 1, 5 and 8 after the onset of the disease (day 0). Y-coordinate indicates blood glycaemia (mg/dl). Grey zone indicates glycaemic range of diagnostic value. X-coordinate indicates time expressed in days from onset of disease. Circles indicate days without insulin administration.

FIG. 9. Clinical score of EAE performed daily for C57BL/6 immunized mice treated with liposomes containing MOG peptide (white circles) or empty liposomes (white triangles). Y-coordinate indicates mean clinical score. X-coordinate indicates time expressed in days post-immunization.

DETAILED DESCRIPTION OF THE INVENTION

In a first aspect the invention provides autoantigen-encapsulating liposomes.

The term "liposome" is to be understood as a self-assembling structure comprising one or more membranes comprised by lipid bilayers, each of which comprises two monolayers containing amphipathic lipid molecules oppositely oriented. Amphipathic lipids comprise a polar (hydrophilic) headgroup region covalently linked to one or two non-polar (hydrophobic) acyl chains. Energetically unfavorable contacts between the hydrophobic acyl chains and the surrounding aqueous medium induce the amphipathic lipid molecules to arrange themselves such that their polar headgroups are oriented towards the bilayer's surface, while the acyl chains reorient towards the interior of the bilayer. An energetically stable structure is thus formed in which the acyl chains are effectively shielded from coming into contact with the aqueous environment.

Liposomes can have a single bilayer membrane (small unilamellar vesicles "SUVs" and large unilamellar vesicles "LUVs"), or multiple bilayer membrane (multilamellar large vesicles "MLVs"). Liposomes may also be prepared as multivesicular vesicles "MVVs", which are liposomes enclosing, or encapsulating, multiple non-concentric aqueous chambers. In contrast, MLVs have multiple concentric "onion-skin"-like membranes, each of which encapsulates an aqueous compartment. Given this encapsulation of aqueous volume within a protective barrier of lipid molecules, liposomes are able to sequester encapsulated molecules, e.g., peptides, away from the degrading effects of factors, e. g., peptidase enzymes, present in the external environment.

Size of the liposomes of the invention is comprised from 500 to 15,000 nm, a size that boosts their uptake by antigen presenting cells. Additionally, the liposomes of the present invention preferably have MVV morphology, as shown in FIG. 1. These large MW liposomes have a significantly higher loading efficiency when compared with conventional MLVs or SUVs, and also favour that the encapsulated active agent, in this case, the autoantigen, is preferably dissolved in the aqueous compartments (instead of precipitating or being anchored to the membranes). All this has advantages in terms of bioavailability of the autoantigen within the antigen presenting cell, which results in a higher immunomodulating activity.

In one embodiment the liposome of the invention has a size comprised from 500 to 12,000 nm. In another embodiment, the size of the liposome is comprised from 500 to 10,000 nm. In another embodiment, the size of the liposome is comprised from 600 to 8000 nm, more particularly from 700 to 7000 nm, or from 800 to 5000 nm, or from 900 to 3000 nm, or from 900 to 2000 nm, or from 900 to 1500 nm, or from 1000 to 1400 nm. In a particular embodiment the liposome has a size comprised from 1000 to 1300 nm, for example 1000 nm, 1050 nm, 1100 nm, 1150 nm or 1200 nm.

In one embodiment the liposome of the invention has MW morphology and a size comprised from 500 to 12,000 nm. In another embodiment, the liposome of the invention has MVV morphology and has a size comprised from 500 to 10,000 nm. In another embodiment, the liposome of the invention has MW morphology and has a size comprised from 600 to 8000 nm, more particularly from 700 to 7000 nm, or from 800 to 5000 nm, or from 900 to 3000 nm, or from 900 to 2000 nm, or from 900 to 1500 nm, or from 1000 to 1400 nm. In a particular embodiment the liposome has MW morphology and a size comprised from 1000 to 1300 nm, for example 1000 nm, 1050 nm, 1100 nm, 1150 nm or 1200 nm.

The liposome membrane may include, without limitation, phospholipids such as phosphatidylcholine ("PC"), phosphatidylserine ("PS"), phosphatidylethanolamine ("PE"), phosphatidylglycerol ("PG"), phosphatidylinositol ("PI")

and phosphatidic acid ("PA"). Other lipids which can constitute the membrane of the nanoparticle include, but are not limited to, cholesterol ("CHOL") and cholesterol-PEG, and fluorescent labeled phosphatidylcholines. The liposome membrane may contain additional molecules not lipidic in nature, such as proteins, carbohydrates, antibodies or polyethyleneglycol (PEG) chains. The liposomes may include particular moieties which are designed to target the liposome to a specific site or target cell, or protect the liposome against a hostile environment (e.g. the gastrointestinal tract). The composition of the liposome is relevant for tolerogenic delivery of the autoantigen. Thus, as mentioned above, the liposome membrane comprises PS in an amount comprised from 10 to 40% by weight with respect to the total membrane liposomal composition. PS contained in the liposomal membrane constitutes an 'eat me' signal that connects PS-recognition by antigen presenting cells with the consequences in tolerance induction. It is noteworthy that the liposome of the invention does not require of further receptors or ligands to be effectively engulfed by DCs and achieve a tolerogenic delivery of the autoantigen. However, other receptors and/or ligands may be assembled into the liposome in order to improve uptake and/or tolerogenic processing.

The term "percentage (%) by weight" refers to the percentage of each component of the liposome membrane in relation to the total weight of the membrane liposomal composition.

By "membrane liposomal composition" it is referred to the totality of membrane bilayers contained in the liposome, for example, when it is a MVV liposome comprising more than one membrane bilayer (as shown in FIG. 1). The same is understood when using the term "liposome membrane" or "liposomal membrane", both of which refer to the totality of membrane bilayers contained in the liposome of the invention (and not only the outer membrane).

In one embodiment the liposome membrane comprises PS in an amount comprised from 15 to 37% by weight with respect to the total membrane liposomal composition. In further embodiments, membrane PS is comprised from 20 to 35%, or from 22 to 35%, or from 22 to 33%, or from 25 to 32%, or from 26 to 31%, or from 27 to 30% by weight with respect to the total membrane liposomal composition, for example 27%, 28%, 29% or 30%. Preferably, membrane PS is 30% by weight with respect to the total membrane liposomal composition.

The liposome according to the present invention may comprise, in addition to PS, variable concentrations of other lipids. In some embodiments, the liposomal membrane also comprises PC. In some embodiments, the liposomal membrane also comprises CHOL. In particular embodiments the liposomal membrane also comprises PC and CHOL.

In one embodiment the liposome membrane comprises PC in an amount comprised from 10 to 40% by weight with respect to the total membrane liposomal composition. In another embodiment the liposome membrane comprises PC in an amount comprised from 12 to 40% by weight with respect to the total membrane liposomal composition. In further embodiments, membrane PS is comprised from 15 to 37%, or from 20 to 35%, or from 22 to 33%, or from 25 to 32%, or from 26 to 31%, or from 27 to 30% by weight with respect to the total membrane liposomal composition, for example 27%, 28%, 29% or 30%.

The amount of CHOL may be comprised from 13 to 53% by weight with respect to the total membrane liposomal composition. In one embodiment, the liposome membrane comprises CHOL in an amount comprised from 20 to 50% by weight with respect to the total membrane liposomal composition. In further embodiments, membrane CHOL is preferably comprised from 27 to 46%, or from 30 to 44%, or from 33 to 42%, or from 36 to 40% by weight with respect to the total membrane liposomal composition, for example 36%, 37%, 38%, 39%, or 40%.

The proportion of the different lipids contained in the liposome membrane must be equilibrated in order to obtain a liposome with appropriate physical and chemical properties in terms of stability, permeability and morphology. In general, the liposomal membrane may comprise PS, PC and CHOL in a molar ratio PS:PC:CHOL which is comprised from 0.6:0.6:0.7 to 1.5:1.5:1.8. The term "ratio" is understood in the usual sense as the magnitude of quantities relative to each other. Specifically, the ratio of two quantities indicates how many times the first quantity (X) is contained in the second quantity (Y), and is expressed as X:Y. The term "molar ratio" is used when the referred magnitude is the molarity. Alternatively, the ratio may be expressed as "weight ratio" when the referred magnitude is weight. Here, ranges of molar ratios are given for the three particular lipids (PS, PC and CHOL). In one embodiment, the membrane comprises a molar ratio PS:PC:CHOL which is comprised from 0.7:0.7:0.8 to –1.4:1.4:1.6. In another embodiment, the membrane comprises a molar ratio PS:PC:CHOL which is comprised from 0.8:0.8:0.9 to 1.2:1.2:1.5. In another embodiment, the membrane comprises a molar ratio PS:PC:CHOL which is comprised from 0.9:0.9:1 to 1.1:1.1:1.4. In a preferred embodiment, the membrane comprises a molar ratio PS:PC:CHOL which is around 1:1:1.33.

As mentioned above, the liposome of the invention encapsulates an autoantigen. The term "autoantigen" refers to a normal protein or complex of proteins that is recognized by the immune system of patients suffering from a specific autoimmune disease. These antigens should, under normal conditions, not be the target of the immune system, but, due to mainly genetic and environmental factors, the normal immunological tolerance for such an antigen has been lost in these patients. In certain embodiments, the liposome encapsulates further autoantigens associated with the same autoimmune disease. For example, the liposome may encapsulate two, three, four or five autoantigens, preferably associated with T1D.

In some embodiments, the weight ratio between the total amount of lipid forming the liposome membrane vs total amount of autoantigen(s) is comprised from 50:1 to 2:1. In another embodiment, the weight ratio between the total amount of lipid forming the liposome membrane vs total amount of autoantigen(s) is comprised from 30:1 to 3:1. In still another embodiment, the weight ratio between the total amount of lipid forming the liposome membrane vs total amount of autoantigen(s) is comprised from 20:1 to 3:1. In still another embodiment, the weight ratio between the total amount of lipid forming the liposome membrane vs total amount of autoantigen(s) is comprised from 15:1 to 3:1. In still another embodiment, the weight ratio between the total amount of lipid forming the liposome membrane vs total amount of autoantigen(s) is comprised from 12:1 to 3:1. In another embodiment, the weight ratio between the total amount of lipid forming the liposome membrane vs total amount of autoantigen(s) is selected from the group consisting of: 11:1, 10:1, 9:1, 8:1, 7:1, 6:1, 5:1 and 4:1.

In one embodiment, the liposome has a size comprised from 500 to 10,000 nm, the liposome membrane comprises 20 to 35% by weight PS and a molar ratio PS:PC:CHOL which is comprised from 0.7:0.7:0.8 to 1.4:1.4:1.6, and the weight ratio between the total amount of lipid forming the liposome membrane vs total amount of autoantigen(s) is comprised from 50:1 to 3:1.

In one embodiment, the liposome has a size comprised from 700 to 7,000 nm, the liposome membrane comprises 22 to 33% by weight PS and a molar ratio PS:PC:CHOL which is comprised from 0.8:0.8:0.9 to 1.2:1.2:1.5, and the weight ratio between the total amount of lipid forming the liposome membrane vs total amount of autoantigen(s) is comprised from 20:1 to 3:1.

In another embodiment, the liposome has a size comprised from 800 to 5000 nm, the liposome membrane comprises 25 to 32% by weight PS and a molar ratio PS:PC:CH which is comprised from 0.9:0.9:1 to 1.1:1.1:1.4, and the weight ratio between the total amount of lipid forming the liposome membrane vs total amount of autoantigen(s) is comprised from 15:1 to 3:1.

In another embodiment, the liposome has a size comprised from 900 to 3000 nm, the liposome membrane comprises 30% by weight PS, 30% by weight PS and 40% by weight CH, and the weight ratio between the total amount of lipid forming the liposome membrane vs total amount of autoantigen(s) is comprised from 12:1 to 3:1, preferably, the weight ratio is selected from the group consisting of: 11:1, 10:1, 9:1, 8:1, 7:1, 6:1, 5:1 and 4:1.

In another embodiment, the liposome has MW morphology and a size comprised from 800 to 5000 nm, the liposome membrane comprises 25 to 32% by weight PS and a molar ratio PS:PC:CH which is comprised from 0.9:0.9:1 to 1.1:1.1:1.4, and the weight ratio between the total amount of lipid forming the liposome membrane vs total amount of autoantigen(s) is comprised from 15:1 to 3:1. In another embodiment, the liposome has MVV morphology and a size comprised from 900 to 3000 nm, the liposome membrane comprises 30% by weight PS, 30% by weight PS and 40% by weight CH, and the weight ratio between the total amount of lipid forming the liposome membrane vs total amount of autoantigen(s) is comprised from 12:1 to 3:1, preferably, the weight ratio is selected from the group consisting of: 11:1, 10:1, 9:1, 8:1, 7:1, 6:1, 5:1 and 4:1. In a preferred embodiment the liposome has MW morphology, 1000 nm, the liposome membrane comprises 30% by weight PS, 30% by weight PS and 40% by weight CH, and the weight ratio between the total amount of lipid forming the liposome membrane vs total amount of autoantigen(s) is comprised from 12:1 to 3:1, preferably, the weight ratio is selected from the group consisting of: 11:1, 10:1, 9:1, 8:1, 7:1, 6:1, 5:1 and 4:1.

The encapsulated autoantigen(s) is(are) associated with a specific autoimmune disease. In certain embodiments, the autoantigen(s) is(are) associated with an autoimmune disease selected from the group consisting of T1D, lupus erythematosus, rheumatoid arthritis, multiple sclerosis, Addison's disease, celiac disease, dermatomyositis, Hashimoto's thyroiditis, myasthenia gravis, pernicious anemia, reactive arthritis, autoimmune hemolitic anemia, autoimmune neutrophenia, Graves' disease, psoriasis, psoriatic arthritis and Sjogren syndrome. In a particular embodiment the liposome encapsulates an autoantigen associated with T1D. Non limiting autoantigens which are known to be associated to T1D are insulin, proinsulin, protein tyrosine phosphatase (IA2, also known as islet cell antigen 512), glutamate decarboxylase (GAD), chromogranin and islet-glucose-6-phosphatase catalytic subunit-related protein (IGRP) (Roep B O, Peakman M. Cold Spring Harb Perspect Med, 2012, vol. 2(4):a007781. oi: 10.1101/cshperspect.a007781.). Thus, in one embodiment the liposome of the invention encapsulates an autoantigen selected from the group consisting of insulin, proinsulin, IA2, GAD, chromogranin and IGRP.

Further, in the sense of the present invention, the autoantigen that is encapsulated in the liposome needs not be the complete antigenic protein. Indeed, specific regions of the relevant proteins have been isolated and described as particularly antigenic. Thus, in certain embodiments the liposome encapsulates an autoantigen that is an antigenic peptide, particularly, an antigenic peptide associated with T1D, for example, antigenic peptides derived from insulin, proinsulin, IA2, GAD, chromogranin and IGRP. For instance, the peptides defined by SEQ ID NO: 1 (21 aa, GIVDQCCTSICSLYQLENYCN) derived from insulin A chain and SEQ ID NO: 2 (30 aa, FVKQHLCGSHLVEALYLVCGERGFFYTPMS) derived from insulin B chain, have been disclosed as particularly autoantigenic in T1D. Thus, in one embodiment the liposome encapsulates an autoantigen associated with T1D and is derived from insulin, preferably selected from the peptides with SEQ ID NO: 1 and SEQ ID NO: 2. In a particular embodiment the liposome encapsulates the peptides with SEQ ID NO: 1 and SEQ ID NO: 2.

Other autoantigenic proteins or peptides that are associated to autoimmune diseases and may be encapsulated in the liposomes of the invention are, for example, peptides from myelin for multiple sclerosis, such as peptides derived from myelin-oligodendrocyte glycoprotein (MOG), peptides from acetylcholine receptor for myasthenia gravis, transglutaminase for celiac disease, thyroglobulin for autoimmune thyroiditis (Lernmark A. J. Clin Invest, 2001, vol. 108, p. 1091-1096). In a particular embodiment the liposome of the invention encapsulates an autoantigen that is an antigenic peptide associated with MS, for example, antigenic peptides derived from MOG, such as the peptide defined by SEQ ID NO: 3.

Autoantigenic peptides contained in the liposomes of the invention are advantageously of a size that enables the direct presentation of said antigens by the major histocompatibility complex surface molecules. By "direct presentation" is meant that no mayor processing of these peptides by the antigen presenting cell is required before surface display. In some embodiments the size of the autoantigenic peptides in the liposomes of the invention is comprised from 5 to 100 amino acids, particularly from 5 to 70 amino acids, or from 8 to 50 amino acids, or from 8 to 35 amino acids, or from 8 to 30 amino acids. Such autoantigens provide advantages in terms of bioavailability, effectiveness of the liposome-based therapy and ease of processing (encapsulation of such small peptides is easier and cheaper when compared with whole proteins or larger peptides).

In one embodiment, the liposome has MW morphology and a size comprised from 700 to 7000 nm, the liposome membrane comprises 22 to 33% by weight PS and a molar ratio PS:PC:CHOL which is comprised from 0.8:0.8:0.9 to 1.2:1.2:1.5, the liposome encapsulates at least one autoantigen that is associated with T1D, preferably an autoantigen which is a peptide derived from insulin, and the weight ratio between the total amount of lipid forming the liposome membrane vs total amount of autoantigen(s) is comprised from 20:1 to 3:1.

In one embodiment, the liposome has MW morphology and a size comprised from 700 to 7000 nm, the liposome membrane comprises 22 to 33% by weight PS and a molar ratio PS:PC:CHOL which is comprised from 0.8:0.8:0.9 to 1.2:1.2:1.5, the at least one autoantigen is a peptide selected from SEQ ID NO: 1 and SEQ ID NO: 2, and the weight ratio between the total amount of lipid forming the liposome membrane vs total amount of autoantigen(s) is comprised from 20:1 to 3:1.

In one embodiment, the liposome has MW morphology and a size comprised from 800 to 5000 nm, the liposome membrane comprises 25 to 32% by weight PS and a molar ratio PS:PC:CHOL which is comprised from 0.9:0.9:1 to 1.1:1.1:1.4, the at least one autoantigen is a peptide selected from SEQ ID NO: 1 and SEQ ID NO: 2, and the weight ratio between the total amount of lipid forming the liposome membrane vs total amount of autoantigen(s) is comprised from 15:1 to 3:1.

In one embodiment, the liposome has MW morphology and a size comprised from 800 to 5000 nm, the liposome membrane comprises 25 to 32% by weight PS and a molar ratio PS:PC:CHOL which is comprised from 0.9:0.9:1 to 1.1:1.1:1.4, the at least one autoantigen is the peptide with SEQ ID NO: 1, and the weight ratio between the total amount of lipid forming the liposome membrane vs total amount of autoantigen(s) is comprised from 15:1 to 3:1.

In one embodiment, the liposome has MW morphology and a size comprised from 800 to 5000 nm, the liposome membrane comprises 25 to 32% by weight PS and a molar ratio PS:PC:CHOL which is comprised from 0.9:0.9:1 to 1.1:1.1:1.4, the at least one autoantigen is the peptide with SEQ ID NO: 2, and the weight ratio between the total amount of lipid forming the liposome membrane vs total amount of autoantigen(s) is comprised from 15:1 to 3:1.

In one embodiment, the liposome has MVV morphology and a size comprised from 700 to 7000 nm, the liposome membrane comprises 22 to 33% by weight PS and a molar ratio PS:PC:CHOL which is comprised from 0.8:0.8:0.9 to 1.2:1.2:1.5, the liposome encapsulates at least one autoantigen that is associated with MS, preferably an autoantigen which is a peptide derived from MOG, such as the peptide defined by SEQ ID NO: 3, and the weight ratio between the total amount of lipid forming the liposome membrane vs total amount of autoantigen(s) is comprised from 20:1 to 3:1.

Various methodologies well-known to those skilled in the art can be used to prepare liposomes which encapsulate one or more peptides. For instance, the liposomes of the invention may be formed by directly entrapping the autoantigen during liposome formation by lipid film hydration method.

In one embodiment, the liposomes of the invention are prepared by a process comprising: (a) preparing a lipid blend in an appropriate solvent, e.g. chloroform, (b) removing the solvent, e.g., by evaporation under vacuum, (c) hydrating the lipid blend with an appropriate buffer, e.g. phosphate buffer saline, containing at least one autoantigen, (d) optionally removing the non-encapsulated peptide, e.g. by centrifugation, and (e) purifying or homogenizing the resulting autoantigen-containing liposomes by size. Preferably, extrusion can be used to size-homogenize liposomes, that is to produce liposomes having a predetermined mean size by forcing the liposomes, under pressure, through filter pores of a defined, selected size. Tangential flow filtration can also be used to purify and regularize the size of liposomes, that is, to produce a population of liposomes having fewer impurities, less size heterogeneity, and a more homogeneous and uniformsize distribution. When the liposome encapsulates more than one autoantigen, the hydrating step (c) is performed in the presence of a buffer containing a mixture of said autoantigens in the desired proportion. Such proportion takes into account the particular encapsulating efficiency for each autoantigen.

In another embodiment, the invention relates to an autoantigen-encapsulating liposome obtained by the method described above.

Other methods known in the art may also be used for obtaining the autoantigen-encapsulating liposomes of the invention. For instance, some embodiments contemplate first obtaining the liposomes and then encapsulating the autoantigen. There are well-known methods in the state of the art to encapsulate a compound within a liposome (see Maurer N. et al., Expert Opin Biol Ther, 2001, vol. 1(6), p. 923-47; Waterhouse D. N. et al., Methods Enzymol., 2005; vol. 391, p. 40-57; Urban P. et al., Nanosc. Res. Lett., 2011, vol. 6, p. 620).

Another aspect of the invention provides a pharmaceutical or veterinary veterinary composition comprising a therapeutically effective amount of the liposome as defined in any one of the preceding claims, together with other appropriate pharmaceutically or veterinary acceptable excipients or carriers.

Preferably, the compositions of the invention comprise liposomes of a narrow particle size distribution, i.e., low size heterogeneity. In a particular embodiment, the pharmaceutical or veterinary composition of the invention comprises liposomes having a size comprised from 700 to 7000 nm, wherein the liposome membrane comprises 22 to 33% by weight PS and a molar ratio PS:PC:CHOL which is comprised from 0.8:0.8:0.9 to 1.2:1.2:1.5, and the weight ratio between the total amount of lipid forming the liposome membrane vs total amount of autoantigen(s) is comprised from 20:1 to 3:1.

Preferably, the liposomes comprised in the composition of the invention encapsulate at least an autoantigen that is associated to T1D. More preferably, the autoantigen is a peptide derived from insulin. Still more preferably, the autoantigen is a peptide selected from SEQ ID NO: 1 and SEQ ID NO: 2.

In one embodiment the liposomes comprised in the composition of the invention encapsulate at least an autoantigen that is associated to MS. Preferably, the autoantigen is a peptide derived from MOG. Still more preferably, the autoantigen is a peptide with SEQ ID NO: 3.

The present invention also contemplates compositions wherein the liposomes encapsulate more than one autoantigen and compositions comprising different liposomes, each encapsulating a different autoantigen. Preferably all autoantigens encapsulated in liposomes in the compositions of the invention are related to the same autoimmune disease, preferably T1D or MS. In a particular embodiment, the composition comprises liposomes encapsulating both peptides with SEQ ID NO: 1 and SEQ ID NO: 2. In another embodiment the composition comprises liposomes encapsulating the peptide with SEQ ID NO: 1 and liposomes encapsulating the peptide with SEQ ID NO: 2. In another embodiment, the composition comprises liposomes encapsulating the peptide with SEQ ID NO: 1 and liposomes encapsulating the peptide with SEQ ID NO: 2 at a liposome with SEQ ID NO: 1 to liposome with SEQ ID NO: 2 weight ration comprised from 10:1 to 1:10, particularly from 5:1 to 1:5, more particularly from 2:1 to 1:2, and preferably 1:1.

In the present invention, the term "pharmaceutically acceptable excipients or carriers" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and animals without excessive toxicity, irritation, allergic response, immunogenicity or other problems or complications commensurate with a reasonable benefit/risk ratio. Likewise, the term "veterinary acceptable" means suitable for use in contact with a non-human animal.

The formulation of the compositions of the invention greatly depends on the administration route. In one embodiment of the invention, the autoantigen-encapsulating liposome is administered to a patient orally. Oral compositions include tablets, powders, capsules, sachets, as well as liquid syrups, suspensions and elixirs, all of which may be formulated by methods well known in the art. The autoantigen-encapsulating liposome can also be administered to a patient by intravenous, intraarterial, intraperitoneal (i.p.), subcutaneous, intramuscular or intradermal route. Compositions adequate for these routes of administration are also well known in the art and include solutions for injection, solutions for perfusion, powder for reconstitution of liquid injections, and pre-filled syringes. In the sense of the present invention it may also be adequate to formulate the autoantigen-encapsulating liposome for intranasal or inhaled administration, rectal administration or for topical administration in the form of, for instance, a cream, a gel, an ointment or a dermal patch. Methods for the preparation of these formulations are known in the art. Further, the autoantigen-encapsulating liposome can be formulated as a controlled release dosage form. Controlled release dosage forms are known in the art and particularly desirable for the treatment of chronic diseases or for the administration of active agents that can be toxic at high doses or that show a low half-life pattern when administered to the patient.

The expression "therapeutically effective amount" as used herein, refers to the amount of a compound that, when administered, is sufficient to prevent development of, or alleviate to some extent, one or more of the symptoms of the disease which is addressed. The particular dose of compound administered according to this invention will of course be determined by the particular circumstances surrounding the case, including the compound administered, the encapsulating efficiency, the route of administration, and similar considerations.

The particular autoimmune condition being treated plays an important role on the particular dose of compound to be administered. In one embodiment, the autoimmune disease to be prevented or treated is selected from the group consisting of T1D, lupus erythematosus, rheumatoid arthritis, multiple sclerosis, Addison's disease, celiac disease, dermatomyositis, Hashimoto's thyroiditis, myasthenia gravis, pernicious anemia, reactive arthritis, autoimmune hemolitic anemia, autoimmune neutrophenia, Graves' disease, psoriasis, psoriatic arthritis and Sjogren syndrome. In a preferred embodiment the autoimmune condition is T1D.

Further, the clinical stage of the autoimmune condition being treated might also need to be taken into account for determining an appropriate dose of autoantigen-encapsulating liposome to be administered. As already mentioned, the liposomes of the invention are useful both for the prevention and the treatment of an autoimmune disease. By "prevention" it is understood to prevent the abnormal immune response to an autoantigen, whereby the pathogenic events underlying the abnormal immune response are not triggered. By "treatment" it is understood dealing with the on-going pathogenic events underlying the abnormal immune response and subsequently ameliorating whichever clinical symptoms are present. This includes treatment of the autoimmune condition in patients that, despite having an autoimmune response and some tissue damage, do not show clinical symptoms or show only few clinical symptoms of the autoimmune disease. This stage is often called "pre-clinical" stage and is typical of most autoimmune diseases, for example in T1D, where it is called prediabetes. In pre-diabetes, pancreatic B cells are damaged to some extent but only some of the diagnostic criteria for diabetes are met. The disease at this stage may be effectively treated with the liposome-based immunotherapy of the invention, as supported by the results obtained in the experiments described below. Additionally, advanced stages of autoimmune disease where tissue damage is high and clinical symptoms are apparent, may also be effectively treated by administering an effective amount of the the autoantigen-encapsulating liposome of the invention.

One embodiment of the invention is directed to the prevention of the autoimmune disease while another embodiment is directed to the treatment of the disease. Another particular embodiment is directed to the treatment of an autoimmune disease during the pre-clinical stage.

In a preferred embodiment the invention provides a liposome or a pharmaceutical or veterinary composition as defined above for use in the prevention of T1D. In another preferred embodiment, the liposome or pharmaceutical or veterinary composition as defined above is for use in the treatment of T1D. In still another a preferred embodiment, the liposome or pharmaceutical or veterinary composition as defined above is for use in the treatment of T1D in a prediabetic subject.

In one embodiment the invention provides a liposome or a pharmaceutical or veterinary composition as defined above for use in the prevention of MS. In another embodiment, the liposome or pharmaceutical or veterinary composition as defined above is for use in the treatment of MS.

Altogether, the dose of autoantigen-encapsulating liposome to be administered is determined in view of several circumstances. Only as an illustrative example, when using MVV liposomes according to the invention containing PS, PC and CHOL at lipid molar ratio 1:1:1.33 (PS:PC:CHOL) which encapsulate TD1-associated autoantigen with SEQ ID NO:1 at lipid to antigen weight ratio 11.6:1 (total amount of lipid vs. total amount of autoantigen), the therapeutically effective amount for treating a human subject suffering from T1D in the pre-diabetic stage can be from 0.05 to 50 mg of autoantigen-encapsulating liposomes/kg of body weight, preferably from 0.5 to 5 mg of autoantigen-encapsulating liposomes/kg of body weight. When SEQ ID NO:2 is encapsulated in liposomes as defined above at lipid to antigen weight ratio 3.8:1 the therapeutically effective amount for treating a human subject suffering from T1D in the pre-diabetic stage can be from 0.05 to 50 mg of autoantigen-encapsulating liposomes/kg of body weight, preferably from 0.5 to 5 mg of autoantigen-encapsulating liposomes/kg of body weight. When using a composition comprising both types of liposomes as defined above, preferably, at a liposome with SEQ ID NO:1 to liposome with SEQ ID NO:2 weight ratio 1:1, the therapeutically effective amount for treating a human subject suffering from T1D in the pre-diabetic stage can also be from 0.05 to 50 mg of autoantigen-encapsulating liposomes/kg of body weight, preferably from 0.5 to 5 mg of autoantigen-encapsulating liposomes/kg of body weight.

Further, the medical expert will determine how many doses of the medicament are administered to the patient in order to prevent or treat the autoimmune disease. In this respect, the inventors have found that only one dose of the autoantigen-encapsulating liposomes of the invention may effectively treat T1D in prediabetic mice. However, the medical expert may decide that more doses are needed to treat advanced stages of the disease. In one embodiment, the liposome or the pharmaceutical or veterinary composition as defined above is for use in the prevention or treatment of an autoimmune disease, preferably T1D, by administering one to five doses of said liposome or pharmaceutical composition to the patient. In a particular embodiment the prevention or treatment is achieved by administering one, two, three or four doses. In another embodiment, the liposome or the pharmaceutical or veterinary composition as defined above is for use in the treatment of T1D by administering one, two, three four or five doses of said liposome or pharmaceutical composition to a patient. In a preferred embodiment, the patient is a prediabetic patient.

Since the preventive or therapeutic effect is achieved through the tolerogenic presentation of the encapsulated autoantigen and subsequent suppression of the autoimmune response, final aspects of the invention relate to a liposome or pharmaceutical or veterinary composition as defined above for restoration of tolerance to self and for suppressing an autoimmune response. In particular embodiments of these aspects of the invention, restoration of tolerance to self and suppression of the autoimmune response are in the context of T1D, more particularly in the context of prediabetes.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

Materials and Methods

Liposome Preparation

Phosphatidylserine (PS) and phosphatidylcholine (PC) were purchased from Lipoid, Steinhausen, Switzerland. Cholesterol (CHOL) was purchased from Sigma Aldrich, Saint Louis, USA. Lipid-conjugated fluorescent dye Oregon Green 488 DHPE was purchased from Invitrogen, California, USA. Alexa Fluor 750 was obtained from Invitrogen in its succinimidyl ester form and was conjugated with the lipid DOPE supplied by Avanti Polar Lipids (Alabaster, USA). Peptides with SEQ ID NO: 1 (GIVDQCCTSICSLYQLE-NYCN) and SEQ ID NO: 2 (FVKQHLCGSHLVEALYL-VCGERGFFYTPMS), which derive from insulin A chain and insulin B chain, respectively, were obtained from Genosphere Biotechnologies (Paris, France) and were >95% pure and trifluoroacetic acid (tfa) removed. Peptide with SEQ ID NO: 3 (YRSPFSRVVHLYRNGK) derived from myelin oligodendrocyte glycoprotein (MOG was obtained from Institut de Recerca Biomédica de Barcelona, IRBB, Barcelone, Spain.

The liposomes were prepared using the thin film hydration method from a lipid mixture of PS, PC and CHOL at 1:1:1.33 molar ratio respectively (Harel-Adar T, 2011). The amount of total lipid was 30 mM. Lipids and lipid-conjugated fluorescent dyes were dissolved in chloroform and the solvent was removed by evaporation under vacuum and nitrogen. The lipids were hydrated with the appropriate buffer (PBS, 0.5 mg/mL solution of peptide with SEQ ID NO: 1 or SEQ ID NO: 2 or SEQ ID NO: 3 in PBS separately), and the liposomes thus obtained were homogenized to 1 µm by means of an extruder (Lipex Biomembranes, Vancouver, Canada). The non-encapsulated peptide was removed from the liposome formulation by centrifugation. Particle size distributions and stability expressed as zeta potential ($\zeta$) of liposomes were measured by dynamic light scattering (DLS) using Malvern Zetasizer, (Malvern Instruments, UK) in undiluted samples. The morphology and lamellarity of the liposomes were examined using cryogenic transmission electron microscopy (cryo-TEM) in a JEOL-JEM 1400 microscope.

Mice

Wild-type NOD mice were obtained from The Jackson Laboratory (Bar Harbor, ME, USA) and kept under specific pathogen-free conditions. Only 8-wk old females were used.

Mice were purchased from Harlan Laboratories (Italy) and housed under conventional conditions. Only 8-10 weeks old females were used. For the induction of EAE, C57BL/6 female mice (Harlan) at age of eight weeks received subcutaneous injections in both flanks of 50 µg MOG peptide in PBS, emulsified in an equal volume of complete Freund's adjuvant (CFA) containing 4 mg/ml of *Mycobacterium tuberculosis* H37RA (Difco, Detroit, MI, USA), under ketamine (50 mg/kg body weight) and xylazine (5 mg/kg body weight). In addition, 250 ng of Pertussis toxin (Sigma Chemical) was injected intravenously at day 0 and 2.

This study was carried out in strict accordance with the recommendations in the Guide for the Care and Use of Laboratory Animals of the Generalitat de Catalunya, Catalan Government. The protocol was approved by the Committee on the Ethics of Animal Experiments of the Germans Trias i Pujol Research Institute (Permit number: DAAM 5157).

Dendritic Cell (DC) Generation and Uptake Experiments

DCs were generated from bone marrow progenitors of NOD mice in culture medium containing GM-CSF (1000 U/ml; Prospec, Rehovot, Israel) as previously reported (Marin-Gallen, Clinical and Experimental Immunology 2010). DCs purity was assessed by CD11c-PECy7 staining (BD Pharmingen) as described (Pujol-Autinell I, et al. PLOS ONE 2013). Viability was determined by annexin and 7aad staining as previously reported (Pujol-Autonell I et al. PLOS ONE, 2013), and cells were counted by flow cytometry (Perfect Count Microspheres, Cytognos, Salamanca, Spain). Liposome capture was performed by co-culturing DCs with liposomal microparticles (empty or loaded with insulin peptides) during 2 hours. Liposomal microparticle stock solution (30 mM) diluted to 100-1000 µM was employed for these experiments. Control DCs were either cultured in basal conditions to obtain immature DCs (iDCs) or stimulated with LPS (100 ng/ml; Sigma) for 24 hours to obtain mature DCs (mDCs). The in vitro uptake of PS-liposomes by DCs was determined with fluorescence labeled PS-liposomes (Oregon green 488 DHPE, Invitrogen). After extensively washing in PBS to remove the liposomes attached to the cell membrane, liposome capture was determined by flow cytometry (FACSCanto II, BD Biosciences).

Tolerogenic Features in DCs after Liposome Capture

Expression of DCs co-stimulatory membrane molecules CD40 and CD86 were determined by Flowcytometry analysis (FACSCanto II). DCs were stained with monoclonal antibodies to mouse CD11c/PE-Cy7, CD40/APC, CD86/PE (BD Pharmingen). Isotype control staining was used as a control. Data were analyzed using CellQuest software (BD Biosciences). Based on previous results of the role of PGE2 in tolerance induction by apoptotic cells (Pujol-Autonell PLOS ONE 8:e63296, 2013), the production of PGE2 after PS-liposome capture by DCs in supernatants of different cultures was assessed by ELISA (PGE2 EIA Kit-Monoclonal; Cayman Chemicals, Ann Arbor, MI). Limit of detection: 80% B/BO: 15 pg/ml. Sensitivity: 50% B/BO: 50 pg/ml. Results were expressed as an index (pg PGE2/106 cells).

T Cell Proliferation Assays

DCs were loaded with 1 mM liposomes (empty or loaded with insulin peptides) during 2 hours with 20 µg/ml of insulin (Sigma, St Louis, MO, USA) and then used to determine T cell proliferation. T cells were obtained after mechanical disruption of NOD spleen and purified by negative selection using antibodies to CD19-PE, CD16/32-PE, CD11c-PECy7 (BD Pharmingen), CD11b-PE (ImmunoTools GmbH, Friesoythe, Germany), and Ly-6G(Gr-1)-eFluor660 (eBioscience, CA, USA) and sorting (FACSAria II, BD Biosciences), as described (Pujol-Autonell, PLOS ONE 2013). DCs (10,000 cells) alone or pulsed with empty PS-liposomes or liposomes encapsulating autoantigen were cultured with 105 T lymphocytes (1:10 ratio). After 6 days, cells were pulsed with 1 µCi of (3H)-thymidine (Perkin Elmer, Waltham, MA, USA) for an additional 16 h. Cells were harvested (Harvester 96, Tomtec Inc., Hamden, CT, USA) and analyzed using a scintillation counter (1450 Microbeta, TriluxWallac, Turku, Finland). T cell proliferation was expressed as c.p.m×103 cells.

Type 1 Diabetes Immunotherapy (Prevention and Treatment)

Pre-diabetic NOD mice (8 weeks old) were given a single intraperitoneal dose of 3 mg of PS-liposomes (empty or encapsulating peptide with SEQ ID NO:1 and SEQ ID NO: 2 at ratio 1:1) in 200 µl saline solution. A sham-control group that only received saline solution was also included. A total of 12-18 animals per group, were used. Mice were monitored daily for urine glucose using Glucocard strips (Menarini, Barcelona, Spain), and weekly for body weight during a 30 week period. Animals with glucosuria were confirmed diabetic when the blood glucose level was >300 mg/dl.

Diabetic NOD mice (>25 weeks old) were i.p. treated with 3 doses of 3.5 mg of PS-liposomes (empty or encapsulating peptide with SEQ ID NO: 1 and SEQ ID NO: 2 at ratio 1:1) in 200 µl saline solution at days 1, 5 and 8 after onset of the disease. Mice were monitored daily for urine glucose using Glucocard strips (Menarini, Barcelona, Spain) during a 30-week period. Animals with glucosuria were confirmed diabetic and the onset of disease was determined when successive blood glucose levels were higher than 200 mg/dL or when a measure was higher than 300 mg/dL. Blood glucose levels were monitored weekly (AccuCheck, Roche Diagnostics, Indianapolis, IN). Daily subcutaneously (s.c.) injected insulin (1 U, Insulatard Flex-Pen, Novo-Nordisk, Bagsvaerd, Denmark) was administered from the onset of disease, unless if normoglycaemia was achieved. Glycaemia was monitored 3 times per week (AccuCheck, Roche Diagnostics, Indianapolis, IN) after fasting for 2 hours.

Insulitis Score

The degree of islet infiltration by leukocytes—insulitis—was determined at the end of the study. Briefly, pancreata from all mice for each group were snap frozen in an isopentane/cold acetone bath. Cryosections of 5 µm were obtained at 5 non-overlapping levels. The sections were stained with Hematoxylin/Eosin, coded and analyzed by 2 independent observers who were blinded to the experimental conditions. Each observer assessed a minimum of 40 islets per animal. Insulitis was scored as described elsewhere (Alba A, J Immunol 2004; 173:6667-75): 0, no insulitis; 1, peri-insular; 2, mild insulitis (<25% of the infiltrated islet); 3, 25-75% of the islet infiltrated; 4, total islet infiltration.

EAE Immunotherapy

C57BL/6 immunized mice are frequently used as model for EAE disease, which is closely related to MS and often serve for testing therapies and treatments against MS. To prevent the development of EAE, C57BL/6 immunized mice were i.p.treated with 2 doses of 1.75 mg of MOG40-55 loaded PS-liposomes in 100 µl of saline solution at days 5 and 9 post immunization. As control, mice were treated with empty liposomes (PS-liposomes) or PBS (sham).

All animals were weighed and examined daily for welfare and clinical status of treated mice as well as neurological signs. Clinical score of EAE was performed according to the following criteria (Espejo C, et al., Exp Neurol 2001): 0, asymptomatic; 0.5, lost of distal half of tail tone; 1, lost of entire tail tone; 1.5, hind limb weakness; 2, hind limb paralysis; 2.5, hind limb paraplegia; 3, forelimb weakness; 4, quadriparesia; 4.5, severe quadriparesis; 5, quadriplegia; and 6, death, as described elsewhere [Espejo 2001, supra]. Clinical follow-up analyses were performed in a blinded manner by two different observers.

Tracking Liposomes after i.p. Administration

For bioimaging experiments, fluorescence labeled PS-liposomes (Alexa Fluor 750) were i.p. injected into prediabetic NOD mice and observed during 3 days. Mice were imaged under anesthesia (Pearl Imager, Li-Cor) at the moment of the administration and 6, 24, 48 and 72 hours after injection. Fluorescence signal was quantified. At the end of the experiment, several organs were obtained, weighted and imaged to determine fluorescence distribution.

Statistical Analysis

Statistics were performed using the Prism 5.0 software (GraphPad software Inc., San Diego, CA). For paired data, a non-parametric Wilcoxon test was performed. Otherwise, Mann Whitney test was used. A p-value <0.05 was considered significant.

Results

PS-Presenting Liposomes Encapsulating Insulin Peptides are Captured by DCs

PS-liposomes were prepared with PS:PC:CHOL at 1:1:1.33 molar ratio, to present the 'death signal' PS on their surface. Empty liposomes present a mean particle size of 1.014 µm which is an optimal size for an efficient uptake by dendritic cells (Ulrich AS, Bioscience Reports 22: 129-150, 2002) with a polydispersity index (PdI) of 0.321. Additionally, zeta potential measurements revealed a net surface charge of −30.66 mV on PS-liposomes. On the other hand, when PS-liposomes encapsulated peptides with SEQ ID NO: 1 or SEQ ID NO: 2 from mouse Insulin2, liposomes show a mean diameter of 1.062 µm (Pd1=0.324) and 0.954 µm (Pd1=0.309) for peptides with SEQ ID NO: 1 and SEQ ID NO: 2 respectively (FIG. 1). Regarding the zeta potential, both encapsulated liposomes present a negative surface charge of −29.5 mV. The % of encapsulation was 44.63±23.68% for peptide with SEQ ID NO: 1 and 88.48±3.97% for peptide with SEQ ID NO: 2 (mean±SD). PS-liposomes encapsulating peptides with SEQ ID NO: 3 had mean diameter of 942.2 nm and zeta potential of −33.66 mV. Encapsulation efficiency for SEQ ID NO: 3 was 89.34±4.69%. By cryo-TEM analysis, it was observed that most liposomes (empty or peptide encapsulating) are multivesicular vesicles (MVV). After co-culture, PS-liposomes were engulfed by DCs (FIG. 2).

DCs have Reduced Expression of Co-Stimulatory Molecules and Produce PGE2 after the Capture of PS-Liposomes Encapsulating Insulin Peptides Viability of DCs after coculture was always similar to control DCs even after a proinflammatory stimulus (FIG. 3A) independently of the dose (range 100-2000 mM, data not shown).

The expression of two co-stimulatory molecules, CD40 and CD86, was assessed on the surface of DCs. (FIG. 3B). It was observed that CD40 and CD86 expression in the cell membrane do not increase after liposome capture, remaining at low levels. After LPS exposure, DCs significantly increase CD40 and CD86 expression and DCs loaded with PS-liposomes significantly increase CD86 ($p<0.001$) but not CD40. By contrast, PSAB-liposomes do not significantly increase CD40 nor CD86 membrane expression.

Based on previous results (Pujol-Autonell, PLOS ONE 2013), the production of PGE2 induced by liposomes in DCs was examined. The concentration of PGE2 was significantly increased in the supernatant of DCs co-cultured with liposomes (empty or loaded with insulin peptides) when compared to iDCs ($p<0.05$) (FIG. 3C).

Impairment of DCs to Stimulate Autologous T Cell Proliferation after Capture of PS-Liposome Encapsulating Insulin Peptides DCs generated from NOD mice bone marrow progenitors were >80% pure, based on staining for the DC marker CD11c, and viability was always >90%. T cell purity and viability were always over 90% and 95% respectively (data not shown). It was observed that the capture of PS- or PSAB-liposomes by iDCs do not increase autologous T cell proliferation when compared to iDCs alone (FIG. 4). After LPS stimulus, T cell proliferation induced by mDCs was higher than proliferation induced by iDCs ($p<0.05$). By contrast, T cell proliferation induced by DCs loaded with PS- or PSAB-liposomes does not increase, even after the effect of these proinflammatory stimuli. The results indicate that the proliferation of T cells induced by PS-liposomes-DCs does not increase, not even after the effect of these proinflammatory stimuli.

PS-Liposomes Encapsulating Insulin Peptides Effectively Treat T1D in NOD Prediabetic Mice To assess the efficacy of liposomes for preventing T1D, we treated NOD mice with a single dose of immunotherapy during the pre-diabetic period (8 weeks old). As expected, animals from the sham-control group developed diabetes from 13 weeks of age and with a final incidence of 81.3% (n=16) (FIG. 5A). The treatment with empty PS-liposomes resulted in a disease incidence of 83.3% (n=18) starting the disease at 15 weeks of age. Treatment with PS-liposomes encapsulating autoantigenic insulin peptides resulted in disease amelioration, with an incidence of 50% (n=12) starting also at 15 weeks of age. No significant differences were found in body weight (FIG. 5B) of mice that received the immunotherapy when compared to sham group or empty liposomes treated group.

Insulitis is Reduced in Mice Treated with PS-Liposomes PS-Liposomes Encapsulating Insulin Peptides Insulitis was scored for 3-6 non-diabetic animals from each group at the end of the follow-up period (30 weeks) to determine any effects of the treatment on islet leukocytic infiltration (FIG. 6A). As expected, animals in the sham group showed high insulitis scores (2.34±0.18). Mice treated with empty PS-liposomes showed a similar insulitis degree (2.12±0.46). Immunotherapy with PS-liposomes encapsulating insulin peptides displayed a biological, although non significant, reduction of insulitis score (1.69±0.58) when compared to sham group. Moreover, the analysis of the percentage of islets classified in each of the five infiltration categories showed that in mice treated with immunotherapy 47% of the islets remained free of insulitis or with peri-insulitis whereas in the sham group and PS-liposomes group, 26% and 34% of the islets were non-destructed respectively (FIG. 6B).

PS-Liposomes Loaded with Insulin Peptides can Revert Diabetes in NOD Mice when Administered after the Onset of the Disease PS-liposomes loaded with insulin peptides reverted diabetes in NOD mice when administered after the onset of the disease (FIG. 8 A). These mice survived without exogenous administration of insulin achieving normal levels of glycaemia. By contrast, mice treated with empty PS-liposomes do not reach normoglycaemia (FIG. 8 B) despite continuous administration of insulin.

PS-Liposomes Encapsulating MOG Peptide Ameliorate EAE

PS-liposomes containing MOG peptide (specific autoantigen in MS) were prepared. These liposomes, when injected i.p. in C57BL/6 immunized mice, prevented the development of the disease (FIG. 9). The treatment with liposomes filled with MOG peptide induced an increase of classical regulatory T cells, a cell population involved in the maintenance of pheripheral tolerance, in the spleen of immunized mice (results not shown). Both PS-liposomes and peptide encapsulation were critical for the therapeutic effect, since empty liposomes had no effect. Thus, MOG peptide-encapsulating PS-liposomes may ameliorate EAE, providing for a less severe first attack and rapid recovery from exacerbation. Consequently, MOG peptide-encapsulating PS-liposomes may be useful for MS treatment.

Tracking Liposomes after i.p. Administration

Fluorescent signal from liposomes was detected in different organs of the immune system. As expected, liposomes were located in the pancreatic lymph nodes, spleen, pancreas and mediastinal or parathymic lymph nodes. (FIG. 7).

REFERENCES CITED IN THE APPLICATION

Marin-Gallen S, Clemente-Casares X, Planas R, Pujol-Autonell I, Carrascal J, et al. "Dendritic cells pulsed with antigen-specific apoptotic bodies prevent experimental type 1 diabetes". Clin Exp Immunol 2010, vol. 160, p. 207-214.

Alba A, Puertas M C, Carrillo J et al. "IFN beta accelerates autoimmune type 1 diabetes in nonobese diabetic mice and breaks the tolerance to beta cells in nondiabetes-prone mice". J Immunol 2004, vol. 173, p. 6667-75.

Pujol-Autonell I, Planas R, Ampudia R, Marin-Gallen S, Sanchez A, Carrascal J, Marin A, Puig-Domingo M, Pujol-Borrell R, Verdaguer J, Vives-Pi M. "Efferocytosis promotes suppresive effects in dendritic cells through prostaglandin E2 production in the context of autoimmunity". PLOS ONE 8:e63296, 2013.

Ulrich AS. "Biophysical aspects of using liposomes as delivery vehicles". Bioscience Reports 2002, vol. 22, p. 129-150.

Maurer N. et al., "Developments in liposomal drug delivery Systems", Expert Opin Biol Ther, 2001, vol. 1(6), p. 923-47.

Waterhouse D. N. et al., "Preparation, characterization, and biological analysis of liposomal formulations of vincristine", Methods Enzymol., 2005; vol. 391, p. 40-57.

Urban P. et al., "Study of the efficacy of antimalarial drugs delivered inside targeted immunoliposomal nanovectors", Nanoscale Research Letters, 2011, vol. 6, p. 620

Roep B O, Peakman M. "Antigen Targets of Type 1 Diabetes Autoimmunity". Cold Spring Harb Perspect Med, 2012, vol. 2(4):a007781. oi: 10.1101/cshperspect.a007781. Review. PMID:22474615.

Lernmark A. "Series introduction: Autoimmune diseases: are markers ready for prediction?". J. Clin Invest, 2001, vol. 108, p. 1091-1096.

Espejo C, et al. "Treatment with anti-interferon-gamma monoclonal antibodies modifies experimental autoimmune encephalomyelitis in interferon-gamma receptor knockout mice". Exp Neurol 2001, vol. 172, p. 460-468

The invention claimed is:

1. A liposome encapsulating one or more autoantigens, wherein
   (i) the liposome has a size from 600 to 8000 nm;
   (ii) liposome membrane lipids consist essentially of:
      (a) phosphatidylserine (PS);
      (b) phosphatidylcholine (PC); and
      (c) cholesterol (CHOL), wherein PS, PC, and CHOL are in relative molar amounts to each other of 0.7-1.4, 0.7-1.4, and 0.8-1.6.

2. The liposome according to claim 1, which is a multi-vesicular vesicle (MVV).

3. The liposome according to claim 1, wherein the weight ratio between the total amount of lipid in the liposome membrane and the total amount of one or more autoantigens is from 50:1 to 2:1.

4. The liposome according to claim 1, wherein the one or more autoantigens have from 5 to 100 amino acids.

5. The liposome according to claim 1, wherein the one or more autoantigens are one or more peptides associated with type 1 diabetes (T1D).

6. The liposome according to claim 5, wherein the one or more autoantigens are selected from the group consisting of the peptides of SEQ ID NO: 1, SEQ ID NO: 2, insulin, proinsulin, protein tyrosine phosphatase 512 (IA2), glutamate decarboxylase (GAD), chromogranin and islet-glucose-6-phosphatase catalytic subunit-related protein (IGRP).

7. A pharmaceutical or veterinary composition consisting of a therapeutically effective amount of liposomes encapsulating one or more autoantigens, and one or more pharmaceutically or veterinary acceptable excipients or carriers, wherein
   (i) the liposomes have a size from 600 to 8000 nm; and
   (ii) liposome membrane lipids consist of phosphatidylserine (PS), phosphatidylcholine (PC), and cholesterol (CHOL), in relative molar amounts to each other of 0.7-1.4, 0.7-1.4, and 0.8-1.6.

8. A method for treating a patient suffering from an autoimmune disease comprising administering a therapeutically effective amount of the liposome encapsulating the one or more autoantigens as defined in claim 1.

9. The method of claim 8, wherein the autoimmune disease is T1D.

10. A liposome encapsulating one or more autoantigens, wherein
    (i) the liposome has a size from 600 to 8000 nm;
    (ii) liposome membrane lipids comprise:
       (a) phosphatidylserine (PS);
       (b) phosphatidylcholine (PC); and
       (c) cholesterol (CHOL), wherein PS, PC, and CHOL are in relative molar amounts to each other of 0.7-1.4, 0.7-1.4, and 0.8-1.6,
    and wherein the liposome consists essentially of the liposome membrane and one or more autoantigens selected from the peptides of SEQ ID NO: 1, SEQ ID NO: 2, insulin, proinsulin, IA2, GAD, chromogranin, and IGRP.

11. The liposome of claim 1 that consists of the liposome membrane and one or more autoantigens selected from the peptides of SEQ ID NO: 1, SEQ ID NO: 2, insulin, proinsulin, IA2, GAD, chromogranin, and IGRP.

12. A pharmaceutical or veterinary composition comprising the liposome of claim 1 and one or more pharmaceutical or veterinary acceptable excipients or carriers.

13. A pharmaceutical or veterinary composition comprising the liposome of claim 10 and one or more pharmaceutical or veterinary acceptable excipients or carriers.

14. A pharmaceutical or veterinary composition comprising the liposome of claim 11 and one or more pharmaceutical or veterinary acceptable excipients or carriers.

* * * * *

UNITED STATES PATENT AND TRADEMARK OFFICE
CERTIFICATE OF CORRECTION

PATENT NO. : 12,048,765 B2  
APPLICATION NO. : 15/111466  
DATED : July 30, 2024  
INVENTOR(S) : Daniel Maspoch Comamala et al.

Page 1 of 1

It is certified that error appears in the above-identified patent and that said Letters Patent is hereby corrected as shown below:

On the Title Page

Left Column, item (71):

Please change the first Applicant's name from "FUNDACIÓ INSTITUT D'INVESTIGACIÓ EN CIENCIES DE LA SALUT GERMANS TRIAS I PUJOL" to --FUNDACIÓ INSTITUT D'INVESTIGACIÓ EN CIÈNCIES DE LA SALUT GERMANS TRIAS I PUJOL--

Please change the second Applicant's name from "FUNDACIÓ INSTITUT CATALÀ DE NANOCIÊNCIA I NANOTECNOLOGIA" to --FUNDACIÓ INSTITUT CATALÀ DE NANOCIÈNCIA I NANOTECNOLOGIA--

Please change the third Applicant's name from "INSTITUCIÓ CATALANA DE RECERCA I ESTUDIS AVANATS" to --INSTITUCIÓ CATALANA DE RECERCA I ESTUDIS AVANÇATS--

Left Column, item (73):

Please change the first Assignee's name from "FUNDACIO INSTITUT D'INVESTIGACIÓ EN CIÈNCIES DE LA SLUT GERMANS TRIAST PUJOL" to --FUNDACIÓ INSTITUT D'INVESTIGACIÓ EN CIÈNCIES DE LA SALUT GERMANS TRIAS I PUJOL--

Please change the third Assignee's name from "INSTITUCIÒ CATALANA DE RECERCA I ESTUDIS AVANCATS" to --INSTITUCIÓ CATALANA DE RECERCA I ESTUDIS AVANÇATS--

Signed and Sealed this  
Seventeenth Day of September, 2024

Katherine Kelly Vidal  
*Director of the United States Patent and Trademark Office*

SEQUENCE LISTING

```
<160> NUMBER OF SEQ ID NOS: 3

<210> SEQ ID NO 1
<211> LENGTH: 21
<212> TYPE: PRT
<213> ORGANISM: Artificial Sequence
<220> FEATURE:
<223> OTHER INFORMATION: peptide derived from insulin A chain

<400> SEQUENCE: 1

Gly Ile Val Asp Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Artificial Sequence
<220> FEATURE:
<223> OTHER INFORMATION: peptide derived from insulin B chain

<400> SEQUENCE: 2

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Met Ser
            20                  25                  30

<210> SEQ ID NO 3
<211> LENGTH: 16
<212> TYPE: PRT
<213> ORGANISM: Artificial Sequence
<220> FEATURE:
<223> OTHER INFORMATION: peptide derived from myelin oligodendrocyte
      glycoprotein

<400> SEQUENCE: 3

Tyr Arg Ser Pro Phe Ser Arg Val Val His Leu Tyr Arg Asn Gly Lys
1               5                   10                  15
```